(12) United States Patent
Wales et al.

(10) Patent No.: US 11,957,330 B2
(45) Date of Patent: Apr. 16, 2024

(54) ENDOSCOPIC SUTURE CINCHING AND CUTTING DEVICE

(71) Applicant: BOSTON SCIENTIFIC SCIMED, INC., Maple Grove, MN (US)

(72) Inventors: Ryan V. Wales, Northborough, MA (US); Christopher R. Deuel, Melrose, MA (US); Kevin L. Bagley, Dedham, MA (US); Kathryn Venuto, Worcester, MA (US); Stan Robert Gilbert, Litchfield, NH (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 367 days.

(21) Appl. No.: 17/089,637

(22) Filed: Nov. 4, 2020

(65) Prior Publication Data
US 2021/0128140 A1 May 6, 2021

Related U.S. Application Data

(60) Provisional application No. 62/930,761, filed on Nov. 5, 2019.

(51) Int. Cl.
*A61B 17/04* (2006.01)
*A61B 17/00* (2006.01)

(52) U.S. Cl.
CPC ...... *A61B 17/0467* (2013.01); *A61B 2017/00367* (2013.01); *A61B 2017/00477* (2013.01); *A61B 17/0469* (2013.01); *A61B 2017/0496* (2013.01)

(58) Field of Classification Search
CPC ............ A61B 17/0467; A61B 17/0469; A61B 2017/00367; A61B 2017/00477; A61B 2017/0496; A61B 2017/0488; A61B 17/0487; A61B 17/0485; A61B 17/0482; A61B 2017/00663; A61B 2017/00659; A61B 2090/037
See application file for complete search history.

(56) References Cited

U.S. PATENT DOCUMENTS 7,993,368 B2  8/2011 Gambale et al.
8,444,673 B2  5/2013 Thielen et al.
(Continued)

FOREIGN PATENT DOCUMENTS

WO    2019226891 A1    11/2019

OTHER PUBLICATIONS

International Search Report and Written Opinion dated Jan. 13, 2021 for International Application No. PCT/US2020/058975.
(Continued)

*Primary Examiner* — Sarah W Aleman
*Assistant Examiner* — Mikail A Mannan
(74) *Attorney, Agent, or Firm* — Seager, Tufte & Wickhem, LLP

(57) ABSTRACT

Medical devices for cinching and cutting one or more suture, and methods for making and using such devices are disclosed. An example medical device may include a shaft, a sleeve attached to the shaft, cutter slidable within the sleeve, a cinch sleeve releasably coupled to the sleeve, and a cinch member. An elongated inner shaft may extend through and be longitudinally movable within the elongated shaft, sleeve, cutter, cinch sleeve, and cinch member. The inner shaft may be actuated to cinch and cut one or more suture disposed within the device.

20 Claims, 28 Drawing Sheets

(56) References Cited

U.S. PATENT DOCUMENTS

| | | |
|---|---|---|
| 8,540,735 B2 | 9/2013 | Mitelberg et al. |
| 8,974,371 B2 | 3/2015 | Durgin et al. |
| 9,486,192 B2 | 11/2016 | Pipenhagen |
| 9,788,831 B2 | 10/2017 | Mitelberg |
| 10,426,457 B2 | 10/2019 | Mitelberg et al. |
| 2011/0196388 A1 | 8/2011 | Thielen et al. |
| 2012/0158023 A1* | 6/2012 | Mitelberg .......... A61B 17/0485 606/144 |
| 2012/0259346 A1 | 10/2012 | Hansen et al. |
| 2018/0028180 A1 | 2/2018 | Binmoeller et al. |
| 2019/0357899 A1 | 11/2019 | Gilbert et al. |
| 2020/0178956 A1 | 6/2020 | Mitelberg et al. |

OTHER PUBLICATIONS

Invitation to Pay Additional Fees dated Jan. 14, 2021 for International Application No. PCT/US2020/058976.

\* cited by examiner

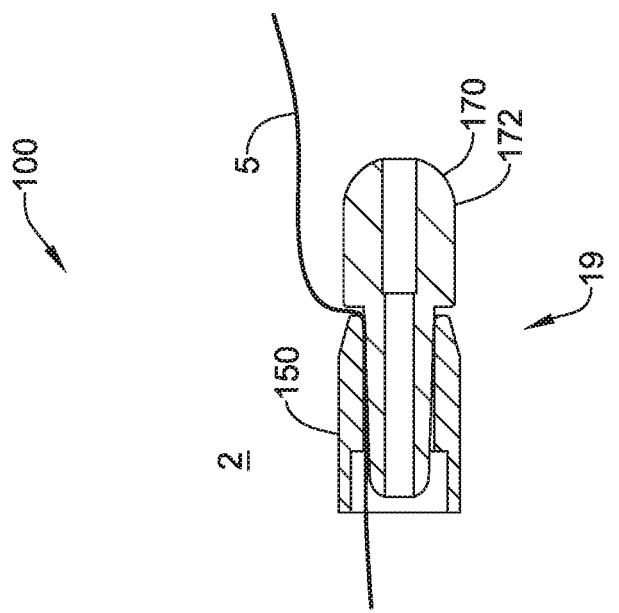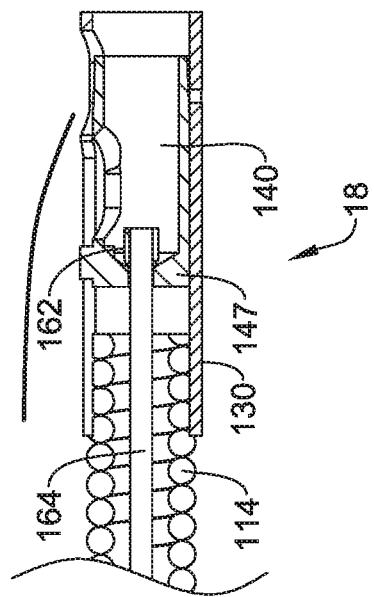
FIG. 5

ENDOSCOPIC SUTURE CINCHING AND CUTTING DEVICE

CROSS REFERENCE TO RELATED APPLICATIONS

The present application claims the benefit of and priority to U.S. Provisional Patent Application Ser. No. 62/930,761, filed on Nov. 5, 2019, titled ENDOSCOPIC SUTURE CINCHING AND CUTTING DEVICE, the disclosure of which is incorporated herein by reference.

TECHNICAL FIELD

The present disclosure pertains to medical devices, and methods for manufacturing medical devices. More particularly, the present disclosure pertains to devices for cinching and cutting a suture, and methods for manufacturing and using such devices.

BACKGROUND

A wide variety of medical devices and methods have been developed for suturing tissue, and securing and/or terminating the free end of a suture relative to the tissue once a suture is in place. These devices are manufactured by any one of a variety of different manufacturing methods and may be used according to any one of a variety of methods. Of the known devices and methods, each has certain advantages and disadvantages. There is an ongoing need to provide alternative devices as well as alternative methods for manufacturing and using such devices.

SUMMARY

This disclosure provides design, material, manufacturing method, and use alternatives for suture termination devices, for example, devices for applying a cinch to a suture. In an example, a medical device for cinching and cutting one or more suture comprises a shaft defining a shaft lumen, a sleeve having a sleeve lumen, the sleeve attached to the shaft, a cutter slidable within the sleeve lumen, a cinch sleeve defining a cinch lumen, the cinch sleeve releasably coupled to the cutter, a cinch member defining a cinch member lumen, the cinch member including at least a proximal portion configured to fit within the cinch lumen, and an inner shaft extending through and longitudinally movable within the shaft lumen, the sleeve lumen, the cinch lumen, and the cinch member lumen, wherein at least one of the cutter and sleeve define a cutting surface, wherein the cutter is slidable between a distal position configured to allow one or more suture to be loaded into the medical device, and a proximal position configured to cut the one or more suture.

Alternatively or additionally to any of the above examples, the cutter has a cutter lumen with a cutter opening extending into the cutter lumen, and the sleeve has a sleeve opening extending into the sleeve lumen, wherein when the cutter is in the distal position, the cutter opening and sleeve opening are aligned, and when the cutter is in the proximal position, the cutter opening is proximal of the sleeve opening.

Alternatively or additionally to any of the above examples, when the cutter is in the distal position, a suture pathway is formed extending through the cinch lumen and cutter lumen, and out through the aligned cutter and sleeve openings.

Alternatively or additionally to any of the above examples, a distal end of the inner shaft is configured to releasably engage the cinch member lumen, wherein proximal longitudinal movement of the inner shaft moves the cinch member from a first configuration in which at least a part of the cinch member is spaced apart from a distal end of the cinch sleeve, to a second configuration in which the proximal portion of the cinch member engages the cinch lumen.

Alternatively or additionally to any of the above examples, the cinch member lumen has a distal section and a proximal section, wherein a diameter of the distal section is larger than a diameter of the proximal section, wherein the distal end of the inner shaft has a diameter larger than the diameter of the proximal section of the cinch member lumen, wherein the distal end is compressible such that application of a predetermined amount of proximal longitudinal force compresses the distal end, allowing it to move into the proximal section of the cinch member lumen.

Alternatively or additionally to any of the above examples, the cutter has a protrusion extending into a lumen of the cutter, the protrusion configured to engage the distal end of the inner shaft, wherein from the second configuration, further proximal longitudinal movement of the inner shaft moves the distal end through and out of the cinch member lumen and into engagement with the protrusion such that continued proximal longitudinal movement of the inner shaft moves the cutter from the distal position to the proximal position and releases the sleeve from the cinch sleeve.

Alternatively or additionally to any of the above examples, the shaft includes a distal compressible coil attached to a proximal end of the cutter, wherein the compressible coil limits distal and proximal movement of the cutter.

Alternatively or additionally to any of the above examples, the medical device further comprising a coupler attached to a distal end of the shaft and a proximal end of the sleeve, the coupler including a cutter stop configured to receive a movement limiter fixed to a proximal end of the cutter in a sliding engagement, wherein distal movement of the cutter is limited by engagement between the movement limiter and the cutter stop.

Alternatively or additionally to any of the above examples, the cinch sleeve is releasably coupled to the sleeve via a releasable connection between the cinch sleeve and the cutter.

Alternatively or additionally to any of the above examples, the cutter has a first snap connector and the cinch sleeve has a second snap connector configured to releasably engage the first snap connector.

Alternatively or additionally to any of the above examples, the cutter has a distal tapered region configured to engage a proximally tapered section of the cinch lumen in a friction fit.

Alternatively or additionally to any of the above examples, the medical device further comprising a compressible spring disposed between a distal end of the cutter and a distal end of the sleeve, wherein when the cutter is in the distal position, the cutter compresses the compressible spring, and when the cutter is in the proximal position the compressible spring is in a biased expanded configuration.

Alternatively or additionally to any of the above examples, the chinch member includes at least one protrusion on the proximal portion and the cinch member includes at least one recess on an inner surface of the cinch member lumen, the at least one recess configured to receive the at least one protrusion to lock the cinch member to the cinch member.

Alternatively or additionally to any of the above examples, the sleeve includes a slot having a first section and a second section, and the cutter includes a pin configured to move between the first and second sections.

Alternatively or additionally to any of the above examples, the pin is in the first section when the cutter is in the distal position, and movement of the pin into the second section causes the cutter to move to the proximal position.

Alternatively or additionally to any of the above examples, movement of the pin from the first section into the second section is achieved by rotating one of the sleeve and cutter relative to the other of the sleeve and cutter.

In another example, a method of cinching and cutting one or more suture comprises inserting one or more suture into a distal end of a cinch sleeve, through a lumen thereof, through a portion of a cutter, and out an opening in a wall of the cutter and an opening in a wall of a sleeve releasably engaged with the cinch sleeve, wherein the cutter is slidable within a lumen of the sleeve, wherein a cutting surface is defined on at least one of the opening in the wall of the cutter and the opening in the wall of the sleeve, inserting a cinch member into the lumen of the cinch sleeve, the cinch member configured to engage the lumen of the cinch sleeve in a friction fit, thereby coupling the cinch member and cinch sleeve and securing the one or more suture between the cinch member and an inner surface of the lumen of the cinch sleeve, and cutting the one or more suture by moving the cutter proximally within the lumen of the sleeve, thereby moving the opening in the cutter proximal of the opening in the sleeve and engaging the cutting surface.

Alternatively or additionally to any of the above examples, inserting the cinch member into the lumen of the cinch sleeve is achieved by moving an inner shaft proximally through the lumen of the cinch sleeve, the lumen of the cutter and the lumen of the sleeve, the inner shaft having a distal end configured to releasably engage the cinch member.

In a further example, a medical device for cinching and cutting one or more suture comprises an elongated shaft defining a shaft lumen, a sleeve having a sleeve lumen and an opening extending into the sleeve lumen, the sleeve attached to the shaft, a cutter at least partially disposed within the sleeve lumen, the cutter releasably connected to the sleeve, the cutter having a cutter lumen and defining a cutting surface, a cinch member defining a cinch member lumen, the cinch member releasably coupled to the cutter, and an inner shaft extending through and longitudinally movable within the shaft lumen, the sleeve lumen, the cutter lumen, and the cinch member lumen, wherein the cinch member and cutter are each slidable between distal positions configured to allow one or more suture to be loaded into the medical device, and proximal positions configured to cut the one or more suture.

Alternatively or additionally to any of the above examples, the cutter is releasably connected to the sleeve by a frangible connection, wherein sliding the cinch member to its proximal position breaks the frangible connection, allowing the cutter to move to its proximal position.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 5 is a side cross-sectional view of the medical device as shown in FIG. 1, in a fourth configuration;

Figure 1:
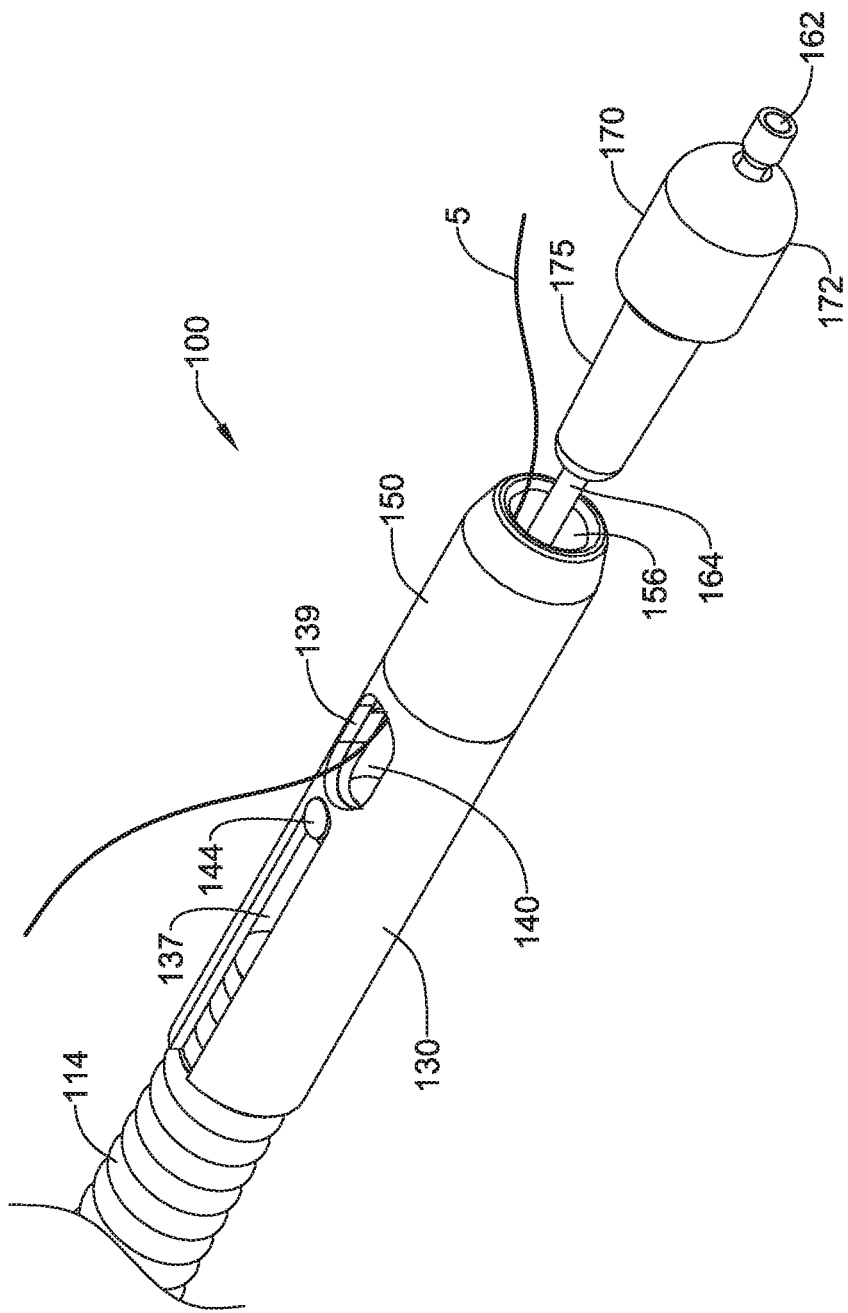
FIG. 1 is a perspective view of a portion of an example medical device for cinching and cutting a suture, in a first configuration.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Medical suturing is used in a number of different interventions. Some of the interventions may include endoscopic suturing at remote sites within the patient and/or otherwise at sites that may be challenging to access. When the suturing process is complete, it may be desirable to terminate the suture in a way that maintains the suture so that the suture does not easily come undone. This may include using a device such as a cinch in order to maintain the suture. Disclosed herein are medical devices that may be used to secure and cut the suture. The medical devices disclosed herein may be delivered through the working channel of an endoscope. At least some of these devices utilize a cinch to maintain the suture. Some example remote sites in which the medical devices disclosed herein may be utilized include, without limitation, the gastro-intestinal (GI) tract, including the stomach, esophagus, and intestines, and within the heart including the heart valves and chambers. Some example procedures in which the devices may be used include, without limitation, gastric bypass, closure of perforations, full thickness resections, closure of post endoscopic submucosal dissection (ESD) sites, gastro jejunal anastomosis and lower esophageal sphincter (LES) repair, stent fixation, bariatric revision and closure of defects, and heart valve repair and replacement. Some additional details of such devices are disclosed herein.

Figure 2:
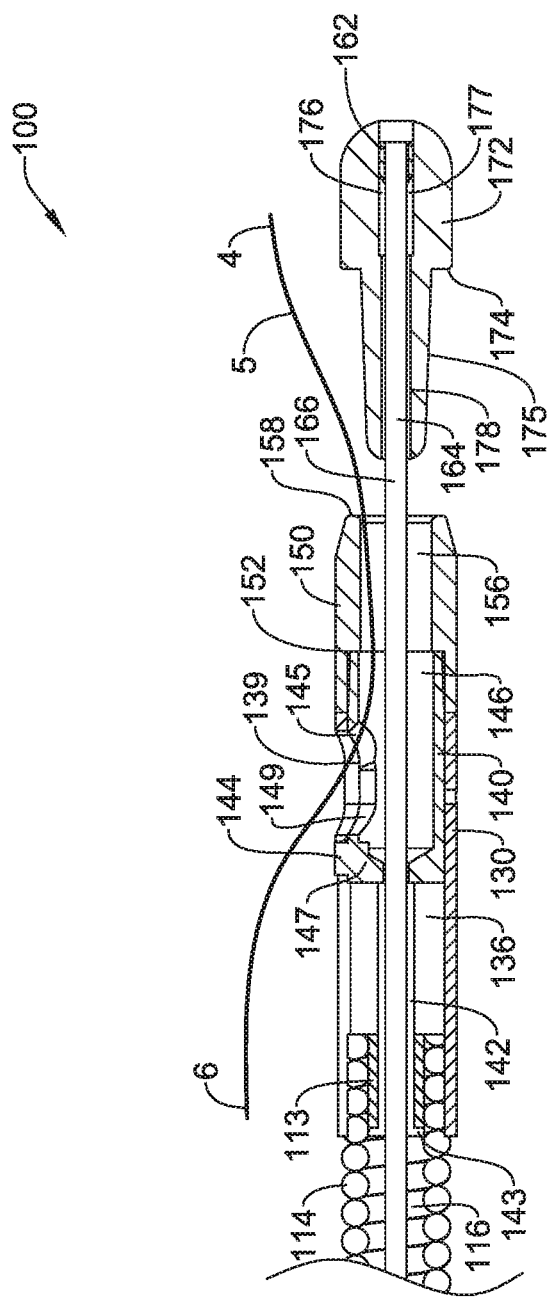
FIG. 2 is a side cross-sectional view of the medical device as shown in FIG. 1, in the first configuration.

FIG. 1 shows a perspective view of a portion of a medical device 100 for cinching and cutting a suture, showing some of the components of the medical device 100, and FIG. 2 shows a side cross-sectional view of the device 100. The medical device 100 may include an elongated shaft 114, a sleeve 130 having a sleeve lumen 136, a cinch sleeve 150 having a cinch lumen 156, and a cinch member 170 having a cinch member lumen 176. An elongated inner shaft 164 may extend through and be longitudinally movable through the shaft lumen 116, sleeve lumen 136, cinch lumen 156, and cinch member lumen 176, as shown in FIG. 2. The elongated inner shaft 164 may be a solid wire, coil, or ribbon, or may be a generally tubular member defining a lumen along a part or the entire length thereof, or a combination of these structures.

The elongated shaft 114 may include and/or be made of an elongated tubular member defining the shaft lumen 116. In the embodiment shown, the elongated shaft 114 is a coiled tubular shaft, however, other configurations are contemplated. For example, the elongated shaft 114 may be a solid metallic or polymer tubular member, a tubular member including and/or made of and/or reinforced with a coil, braid and/or mesh material, or the like. Further, the elongated shaft 114 may include one or more slots and/or grooves and/or channels formed therein, for example, to enhance the flexibility characteristics thereof. The elongated shaft 114 may include or be made of one or more metals, polymers, and/or composite or layered or reinforced structures thereof, including any of those disclosed herein.

In some examples, the elongated shaft 114 may be attached directly to the sleeve 130 by threading, adhesive, welding, soldering, or other suitable connection method. the sleeve 130 may have an opening 139 extending into the sleeve lumen 136. In some examples, the opening 139 may be positioned adjacent the distal end of the sleeve 130, as shown in FIG. 1. The sleeve 130 may further include a slot 137 extending into the sleeve lumen 136.

The cinch sleeve 150 may have a cinch lumen 156 and a proximal end in contact with the distal end of the sleeve 130. The proximal end of the cinch lumen 156 may include a tapered region 152 configured to receive the distal end of the cutter 140 in an interference fit. In other examples, the tapered region 152 may define an inner shoulder configured to receive the distal end of the cutter 140. The inner shoulder may limit proximal movement of the cutter 140 through the cinch sleeve 150.

The cutter 140 may include an opening 149 into the cutter lumen 146. The opening 149 may define a cutting surface 145. In some examples, the cutting surface 145 is disposed on the distal edge of the opening 149. The cutter 140 may be slidably disposed within the sleeve 130. In the first configuration, shown in FIG. 2, the distal portion of the cutter 140 engages the inner shoulder 152 of the cinch sleeve 150. The cutter 140 may include an inner protrusion 147 extending into the cutter lumen 146 at the proximal end of the cutter 140. The inner protrusion 147 may be configured to allow the inner shaft 164 to pass through but prevent an enlarged distal region 162 of the inner shaft 164 from passing proximally therethrough. In some examples, the proximal end of the cutter 140 may include an outwardly extending pin 144 configured to slide within the slot 137 in the sleeve 130, as shown in FIG. 1. The pin 144 may prevent the cutter 140 from rotating within the sleeve 130, and keep the opening 149 aligned with the opening 139 in the sleeve 130.

In other examples, the cutter 140 may have a movement limiter 142 configured to limit distal movement of the cutter 140 within the sleeve 130. In the example shown in FIG. 2, the movement limiter 142 is a hypotube fixed to the proximal end of the cutter 140 and slidable over the inner shaft 164. The proximal end of the movement limiter 142 may include a projection 143 configured to engage a cutter stop 113 fixed within the distal end of the shaft 114. When the projection 143 engages the proximal end of the cutter stop 113, the cutter 140 is prevented from further distal movement. The cutter stop 113 may include a groove or recess configured to receive the projection 143 and limit rotation of the cutter 140 within the cinch sleeve 150. In some examples, the cinch sleeve 150 may not have a tapered lumen or an inner shoulder 152 and instead have a cylindrical lumen 156 which would allow the cutter 140 to move distally all the way through the cinch sleeve 150. When the pin 144 is not present, the projection 143 prevents the cutter 140 from moving distally all the way out of the cinch sleeve 150. Proximal movement of the cutter 140 is stopped when the proximal end of the cutter 140 abuts the distal end of the shaft 114. In general either the pin 144 and slot 137 or the movement limiter 142 and cutter stop 113 are present and serve to limit rotation and proximal movement of the cutter 140 within the cinch sleeve 150, however in some examples, all of the elements may be present.

The cinch member 170 may be configured to engage the cinch sleeve 150 to secure the suture 5. The cinch member 170 may include a distal head 172 with a diameter greater than the diameter of the cinch lumen 156, as shown in FIG. 2. The distal head 172 may have a proximally facing shoulder surface 174. The transition between the diameters of the distal head 172 and a proximal portion 175 may occur rapidly, defining a generally stepped shoulder portion having a rapid and/or stepped increase in outer diameter, as shown in FIG. 2. However, in other embodiments, the transition in diameters may be tapered and/or angled gradually and/or in a stepwise fashion such that the outer diameter increases in size in a distal direction in a more gradual manner, and a more subtle shoulder may be defined. In such embodiments, the widened diameter portion and/or shoulder may simply be defined by a distal head 172 that includes an outer diameter sized such that it cannot fit into the cinch lumen 156 of the cinch sleeve 150.

The cinch member 170 may have a proximal portion 175 configured to fit within the cinch lumen 156 in a friction fit. The cinch lumen 156 may have a tapered or constant inner diameter. The proximal portion 175 is configured and/or designed to mate with the cinch lumen 156 to trap and/or wedge a portion of a suture 5 therebetween. As such, the cinch member 170, in combination with the cinch sleeve 150, make up the "cinch" that will be applied to the suture. The cinch member 170 may have a cinch member lumen 176 extending at least partially therethrough. The cinch member lumen 176 may have a distal section 177 and a proximal section 178. The diameter of the distal section 177 may be larger than the diameter of the proximal section 178. In the example shown in FIGS. 1-5, the cinch member lumen 176 extends completely through the cinch member 170, however, this is not necessary. In some examples, the cinch member lumen 176 may extend only through the proximal portion 175, with the distal head 172 being solid and devoid of any lumen. In this embodiment, the distal end of the inner shaft 164 may be bonded to the lumen 176 with a frangible bond that may be broken by a predetermined proximal force once the cinch member 170 is pulled into the cinch sleeve 150.

The inner shaft 164 may include an enlarged distal region 162 and a proximal region 166. The enlarged distal region 162 and proximal region 166 may be a single monolithic piece, or the enlarged distal region 162 may be a separate element that is connected to the proximal region 166. The enlarged distal region 162 may be sized to engage the cinch member lumen 176. The diameter of the enlarged distal region 162 may be larger than the diameter of the proximal region 166. The diameter of the enlarged distal region 162 may be slightly larger than the proximal section 178 of the cinch member lumen 176 to provide an interference fit. In some examples, the enlarged distal region 162 may be compressible or deformable such that the application of a predetermined amount of proximal longitudinal force allows the interference fit to be overcome, thereby allowing the enlarged distal region 162 to be pulled through the narrower proximal section 178 of the cinch member lumen 176. In other examples, the enlarged distal region 162 may be rigid and the lumen 178 may be deformable to allow the enlarged distal region 162 to be pulled proximally through the cinch member 170. In the first configuration, the enlarged distal region 162 of the inner shaft 164 may be disposed within the distal section 177 of the cinch member lumen 176 and the proximal region 166 is disposed within the proximal section 178 of the cinch member lumen 176, as shown in FIG. 2.

FIGS. 2-5 illustrate the steps involved in securing and cutting a suture using the medical device 100. The medical device 100 is assembled into the deployment or first configuration shown in FIGS. 1 and 2. In the first configuration, the inner shaft 164 may extend through the shaft 114, the sleeve 130, cutter 140, cinch sleeve 150, and cinch member 170. The enlarged distal region 162 of the inner shaft 164 may be disposed within the distal section 177 of the cinch member lumen 176, within the distal head 172, holding the cinch member 170 distally away from the distal end 158 cinch sleeve 150.

The cutter 140 is disposed in a distalmost position, with its distal end abutting the inner shoulder 152 of the cinch sleeve 150 such that the opening 149 of the cutter 140 is aligned under the opening 139 in the sleeve 130. This places the pin 144 at the distal end of the slot 137, as shown in FIG. 1.

With the device 100 in the first configuration, the device 100 may be loaded with a suture 5 and be used to apply a cinch to the suture 5. For example, following a suturing procedure in which a first end 4 of the suture 5 is disposed within the tissue, the second, or free end 6 of the suture 5 may be loaded into and/or through the device 100. The proximal end of the suture may be fed into the distal end 158 of the cinch sleeve 150, through the cinch lumen 156 and the cutter lumen 146, and out through the aligned openings 149, 139 in the cutter 140 and sleeve 130, respectively. This may be done with or without using a tool or guide, such as a tubular guide, wire, loop, needle, or the like.

In the example shown in FIGS. 1 and 2, the entire cinch member 170 is positioned distal of the cinch sleeve 150. In other examples, the distal head 172 and at least part of the proximal portion 175 of the cinch member 170 are positioned distal of the distal end 158 of the cinch sleeve 150 such that sufficient space exists between the proximal portion 175 of the cinch member 170 and the inner surface of the cinch lumen 156 to thread the suture 5 through the cinch lumen 156 and cutter lumen 146 to the openings 149, 139.

Figure 3:
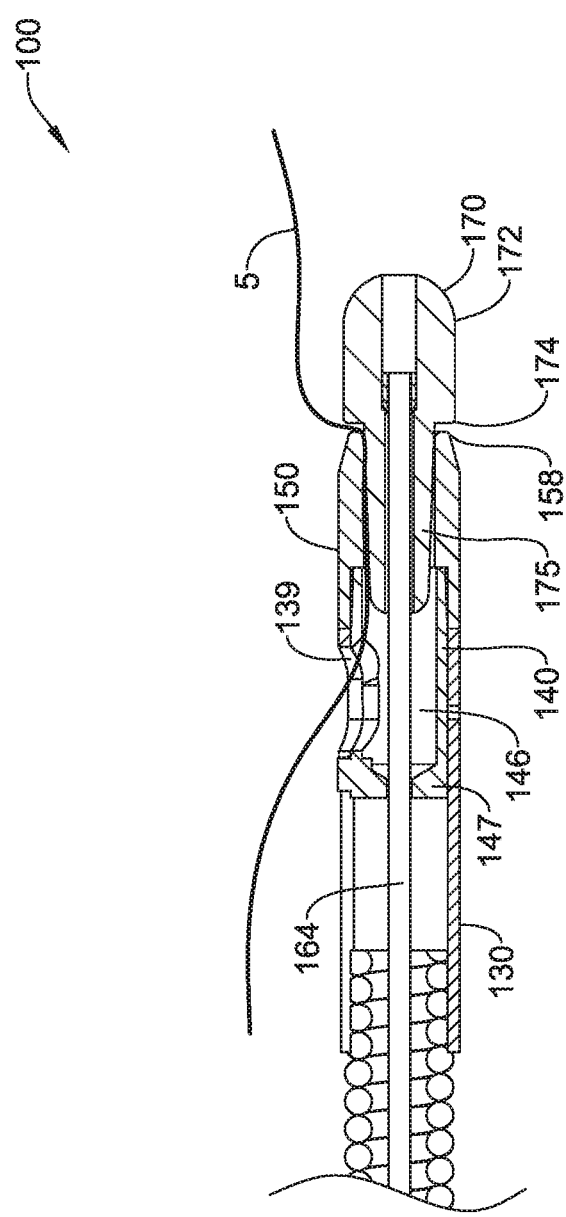
FIG. 3 is a side cross-sectional view of the medical device as shown in FIG. 1, in a second configuration.

Once the suture 5 is disposed within the cinch lumen 156, the suture 5 may be secured by moving the cinch member 170 into the cinch lumen 156. This may be achieved by pulling the inner shaft 164 proximally. A first stage of proximal longitudinal movement of the inner shaft 164 pulls the engaged cinch member 170 into the cinch lumen 156 of the cinch sleeve 150 until the proximal portion 175 of the cinch member 170 engages the inner surface of the cinch sleeve 150, thereby compressing and securing the suture 5, moving the device 100 into a second configuration as shown in FIG. 3. The interference fit between the proximal portion 175 and the inner surface of the cinch lumen 156 secures the suture 5 even when there is a gap between the proximally facing shoulder surface 174 and the distal end 158 of the cinch sleeve 150. This gap may prevent crimping and possible damage to the suture as it bends at an approximately right angle. However, in other examples, the cinch member 170 may be pulled proximally until the proximally facing shoulder surface 174 engages the distal end 158 of the cinch sleeve 150, thereby providing an additional securement point. In such an example, the edges of the proximally facing shoulder surface 174 and the distal end 158 of the cinch sleeve 150 are generally smooth to prevent damage to the suture.

In a second stage of proximal longitudinal movement, the inner shaft 164 may then be pulled further proximally, pulling the inner shaft 164 through and proximally out of the cinch member 170. This proximal movement of the inner shaft 164 may expand the deformable proximal section 178 of the cinch member lumen 176 as the enlarged rigid distal region 162 moves proximally, allowing the inner shaft 164 to move completely through and out of the cinch member lumen 176, disengaging the inner shaft 164 from the cinch member 170. The enlarged distal region 162 moves through the lumen 146 of the cutter 140 until it engages the inner protrusion 147. Further proximal movement of the inner shaft 164 pulls the cutter 140 proximally.

A shear edge or cutting surface 145 may be defined on the distal edge of the opening 149 in the cutter 140. In some embodiments, a cutting surface may also be defined on the proximal edge of the opening 139 in the sleeve (not shown). With the enlarged distal region 162 of the inner shaft 164 seated against the inner protrusion 147, further proximal movement of the inner shaft 164 pulls the cutter 140 proximally into a third configuration, compressing the suture 5 between the proximal end of the opening 139 and the cutting surface 145, which cuts the suture 5, as shown in FIG. 4.

Figure 4:
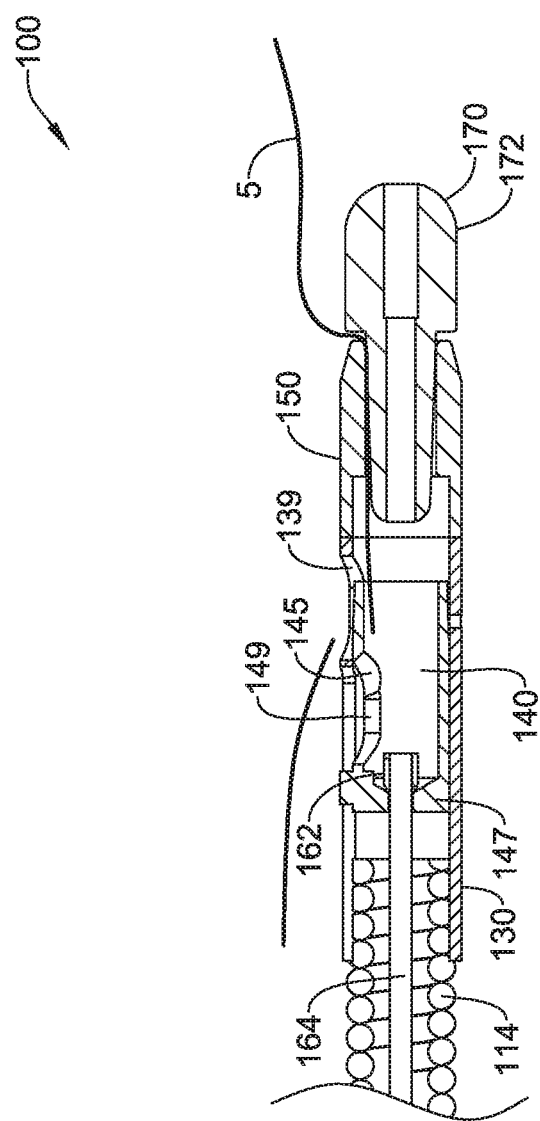
FIG. 4 is a side cross-sectional view of the medical device as shown in FIG. 1, in a third configuration.

From the third configuration shown in FIG. 4, a third stage of proximal longitudinal movement of the inner shaft 164 may disengage the sleeve 130 and cutter 140 from the cinch sleeve 150 as shown in FIG. 5. The inner shaft 164 is pulled proximally with sufficient force to overcome the friction fit between the sleeve 130 and cinch sleeve 150. The shaft 114, sleeve 130, cutter 140, and inner shaft 164 remain connected to one another, forming a shaft assembly 18, which may be removed from the body. The cinch member 170 and cinch sleeve 150 form a cinch assembly 19, and may be left in place adjacent the tissue 2 with the secured suture 5, as shown in FIG. 5. The suture 5 is embedded in the tissue 2 and secured adjacent the tissue 2 by the cinch assembly 19.

Figure 6:
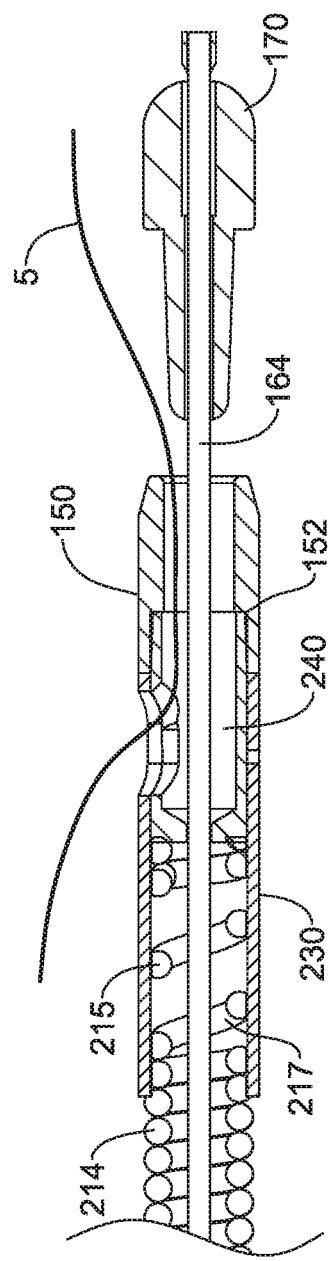
FIG. 6 is a side cross-sectional view of a portion of another example medical device for cinching and cutting a suture.

FIG. 6 shows an alternate shaft 214, sleeve 230, and cutter 240 that may be used with the cinch sleeve 150, cinch member 170, and inner shaft 164 described above. This embodiment utilizes a coil 215 at the distal end of the shaft 214 as a means of preventing the cutter 240 from advancing out the end of the sleeve 230. The coil 215 may be a separate element attached to the distal end of the shaft 214, or the coil 215 may be the distal end region of a monolithic shaft 214, with the distal end region formed as a spring region 217 with spaces between coil windings. The distal end of the coil 215 may be permanently attached to the cutter 240 such as by welding, adhesive, or other permanent connection. The coil 215 acts as a compression spring. The coil 215 may also properly position the cutter 240 for coupling to the cinch sleeve 150. The cutter 240 may be the same as the cutter 140 described above except the cutter 240 may be devoid of the pin 144. The sleeve 230 may be the same as the sleeve 130 described above except the sleeve 230 may be devoid of the slot 137. Distal movement of the cutter 240 may be limited by the inner shoulder 152 of the cinch sleeve 150 and/or the expanded position of the coil 215. The sleeve 230 is removably coupled to the cinch sleeve 150.

As with the medical device 100 described above, the cinch member 170 is pulled proximally into the cinch sleeve 150 by pulling the inner shaft 164 proximally, the enlarged distal region 162 may be deformed, allowing the inner shaft 164 to be pulled completely through the cinch member 170. As the inner shaft 164 is pulled further it contacts the inner protrusion 147 on the cutter 140. As the inner shaft 164 pulls against the inner protrusion 147, the inner shaft 164 pulls the cutter 140 proximally, compressing the coil 215, cutting the suture and uncoupling the cutter 140 and sleeve 130 from the cinch sleeve 150. The inner shaft 164 may then be released, allowing the coil 215 to return to its biased expanded configuration and causing the cutter 140 to go back to its original location. The proximal end of the sleeve 130 may be permanently attached to the outside of the coil 215, proximally of the spring region 217. The proximal face of the cutter 140 may also be permanently attached to the coil 215. The coil spacing between the cutter 140 and proximal end of sleeve behaves like a compression spring.

Figure 7:
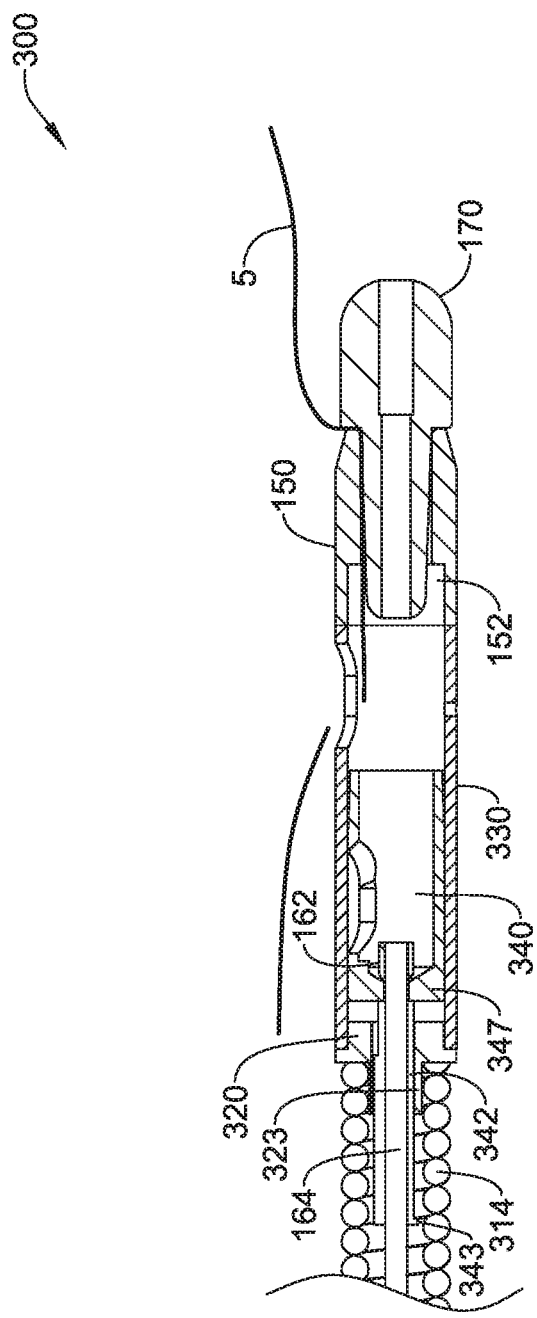
FIG. 7 is a side cross-sectional view of a portion of another example medical device for cinching and cutting a suture.

FIG. 7 shows another example of shaft 314, sleeve 330, and cutter 340 that may be used with the cinch sleeve 150, cinch member 170, and inner shaft 164 described above. The cinch member 170 is shown positioned completely within the cinch sleeve 150, however, as discussed above with regard to FIG. 3, in some examples, the cinch member 170 may secure the suture 5 when a gap remains between the head of the cinch member 170 and the distal end of the cinch sleeve 150. The embodiment shown in FIG. 7 utilizes a coupler 320 fixed to the distal end of the shaft 314 and the proximal end of the sleeve 330 as a means of limiting proximal and distal movement of the cutter 340. The coupler 320 may include a proximally extending cutter stop 323 disposed within the shaft 314. The cutter 340 may include a movement limiter 342 configured to limit both the proximal and distal movement of the cutter 340 within the sleeve 330. In the example shown in FIG. 7, the movement limiter 342 is a hypotube fixed to the proximal end of the cutter 340 and slidable over the inner shaft 164 and within the cutter stop 323 on the coupler 320. The proximal end of the movement limiter 342 may include an outward projection 343 configured to engage the cutter stop 323 on the coupler 320 when the cutter 340 is moved distally.

When the projection 343 engages the cutter stop 323, the cutter 340 is prevented from further distal movement. In some examples, the cinch sleeve 150 may not have an inner shoulder 152 and instead have a cylindrical lumen 156 which would allow the cutter 340 to move distally all the way through the cinch sleeve 150. The projection 343 prevents the cutter 340 from moving distally all the way out of the cinch sleeve 150. The distal end of the coupler 320 engages the proximal end of the cutter 340, limiting the proximal movement of the cutter 340.

The cutter 340 may be the same as the cutter 140 described above except the cutter 340 may be devoid of the pin 144. The sleeve 330 may be the same as the sleeve 130 described above except the sleeve 330 may be devoid of the slot 137. The sleeve 330 is removably coupled to the cinch sleeve 150.

As with the medical device 100 described above, the cinch member 170 is pulled proximally into the cinch sleeve 150 by pulling the inner shaft 164 proximally, the enlarged distal region 162 may be deformed, allowing the inner shaft 164 to be pulled completely through the cinch member 170. As the inner shaft 164 is pulled further it contacts the inner projection 347 on the cutter 340. As the inner shaft 164 pulls against the inner projection 347, the inner shaft 164 pulls the cutter 340 proximally, cutting the suture 5. Once the proximal end of the cutter 340 engages the coupler 320, further proximal movement of the inner shaft 164 causes the sleeve 330 to be uncoupled from the cinch sleeve 150.

Figure 8:
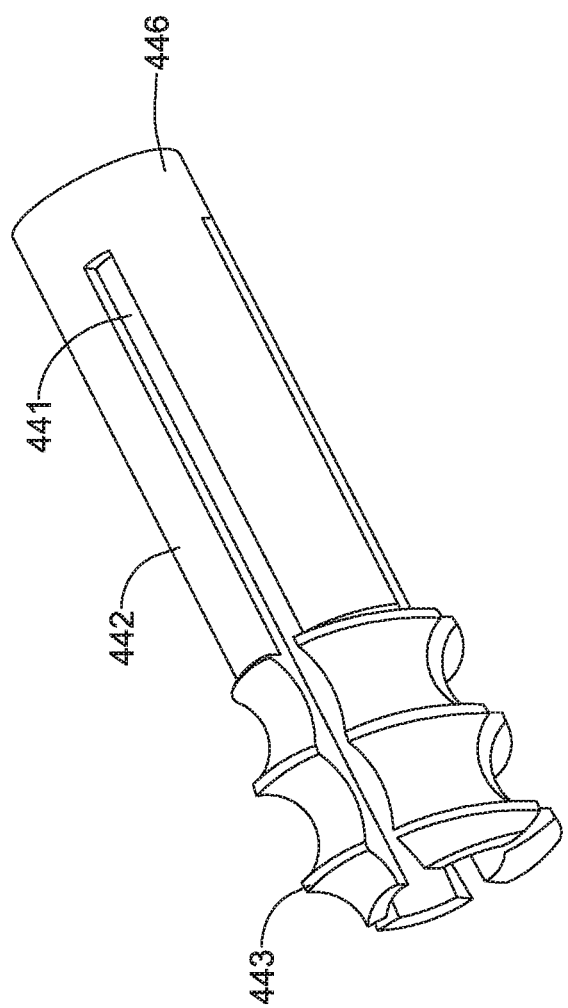
FIG. 8 is a perspective view of an example helical connector.
Figure 9:
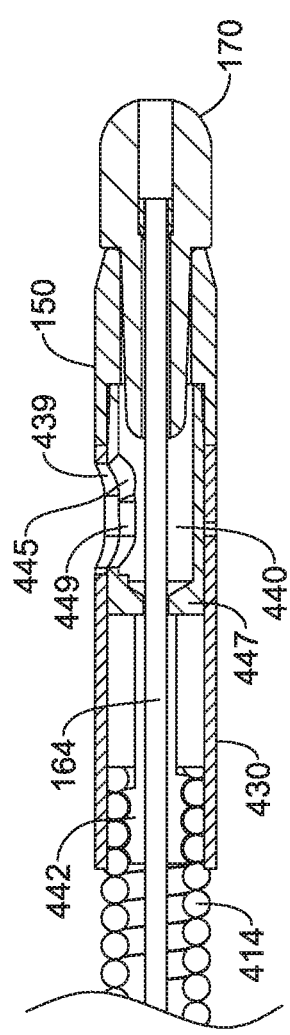
FIG. 9 is a side cross-sectional view of a portion of an example medical device for cinching and cutting a suture including the helical connector of FIG. 8.

FIG. 8 is a perspective view showing an alternative helical connector 442 having a distal end 446 attached to the proximal end of the cutter 440, as shown in FIG. 9. The helical connector 442 may have a helical proximal portion 443 and one or more slots 441 extending from the proximal end towards the distal end 446. The slots 441 allow the proximal portion 443 to be deflected inwards. The helical connector 442 is configured to slide over the inner shaft 164 as shown in FIG. 9. The helical proximal portion 443 is configured to engage the inner surface of a helical coil shaft 414, allowing the helical connector 442 to move axially within the shaft 414, with the proximal portion 433 being deflected inward as it moves over the inner surface of the coil shaft 414.

The cutter 440 may be the same as the cutter 140 described above except the cutter 440 may be devoid of the pin 144. The sleeve 430 may be the same as the sleeve 130 described above except the sleeve 430 may be devoid of the slot 137. The sleeve 430 is removably coupled to the cinch sleeve 150.

As with the medical device 100 described above, the cinch member 170 is pulled proximally into the cinch sleeve 150 by pulling the inner shaft 164 proximally. The enlarged distal region 162 may be deformed, allowing the inner shaft 164 to be pulled completely through the cinch member 170. As the inner shaft 164 is pulled further it contacts the inner projection 447 on the cutter 440. As the inner shaft 164 pulls against the inner projection 447, the inner shaft 164 pulls the cutter 440 proximally, with the helical proximal portion 443 of the helical connector 442 causing the cutter 440 to rotate, pinching the suture between the cutting surface 445 and the opening 439 on the sleeve 430, and cutting the suture 5. The cutting surface 445 may be disposed along the sides of the opening 449. Once the proximal end of the cutter 440 engages the distal end of the shaft 414, further proximal movement of the inner shaft 164 causes the sleeve 430 to be uncoupled from the cinch sleeve 150.

Figure 10:
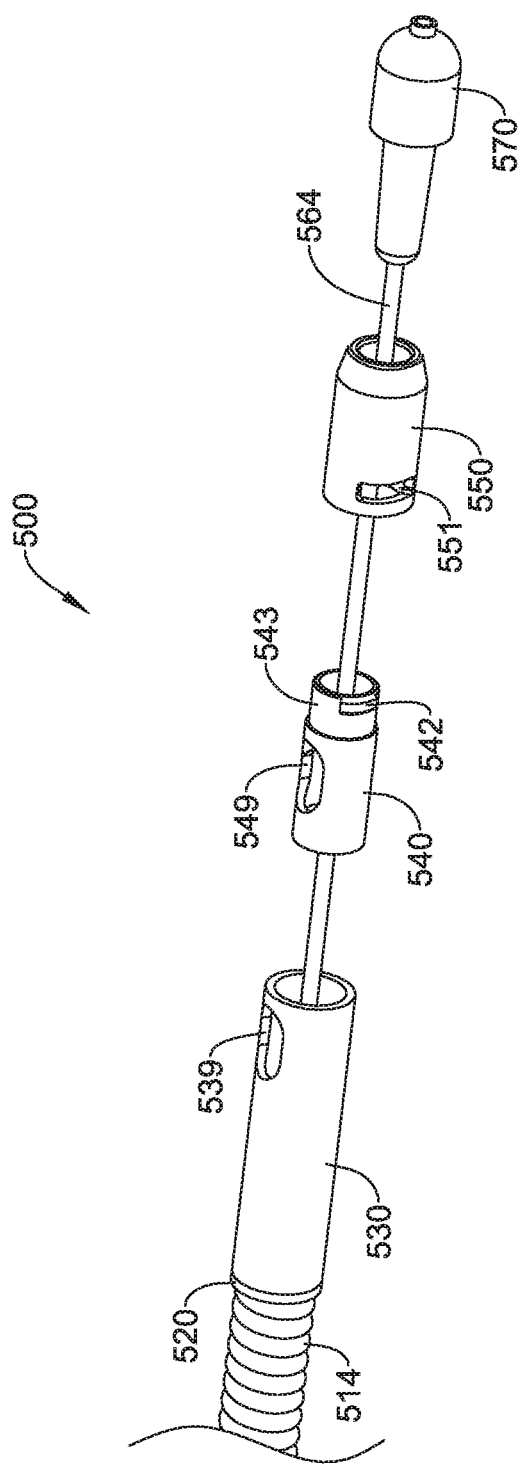
FIG. 10 is a perspective exploded view of a portion of another medical device for cinching and cutting a suture.
Figure 11:
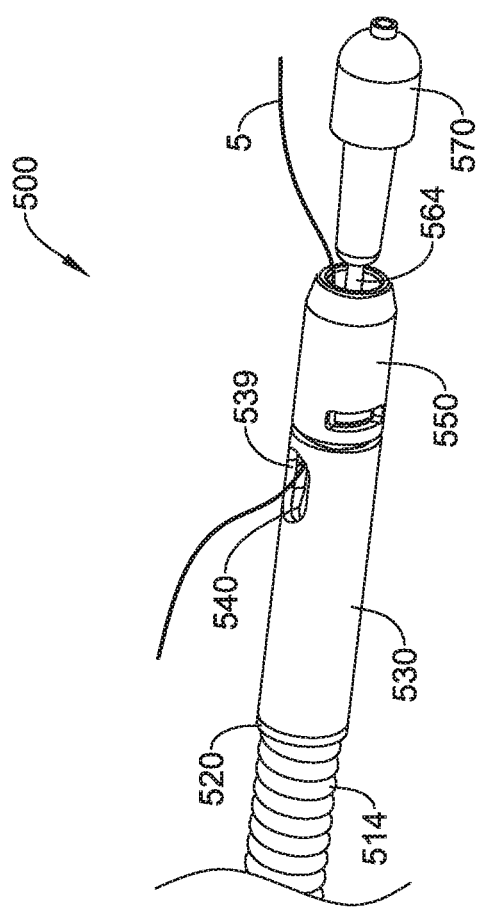
FIG. 11 is a perspective view of the medical device as shown in FIG. 10, in a first configuration.
Figure 12:
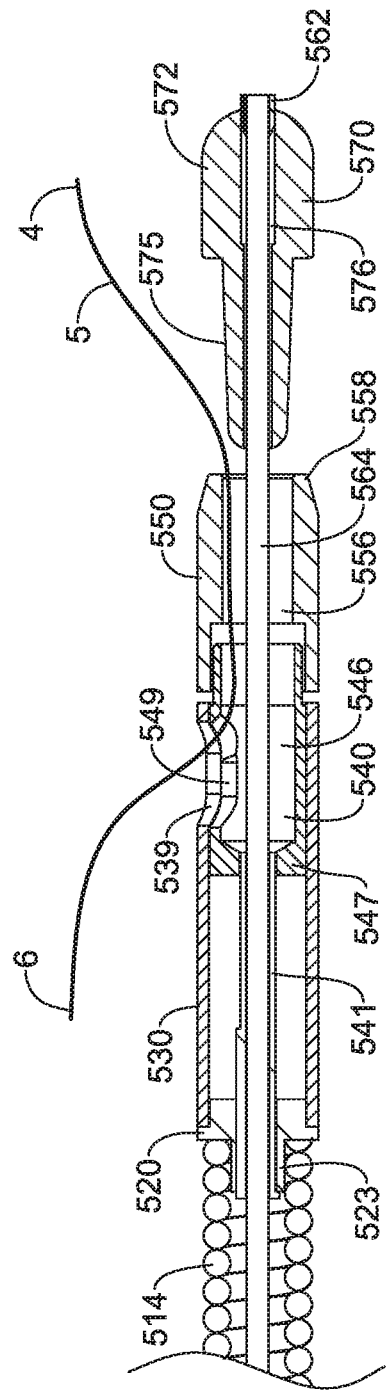
FIG. 12 is a side cross-sectional view of the medical device as shown in FIG. 10, in the first configuration.
Figure 13:
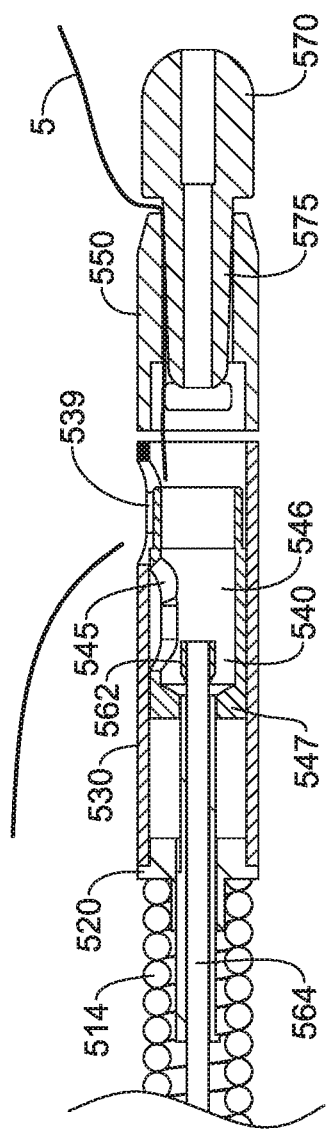
FIG. 13 is a side cross-sectional view of the medical device as shown in FIG. 10, in a second configuration.

FIGS. 10-13 illustrate another example medical device 500 for securing and cutting a suture. FIG. 10 shows a partial exploded view of the medical device 500, FIGS. 11 and 12 show the medical device 500 in an open or first configuration, allowing a suture 5 to be inserted, and FIG. 13 shows the medical device 500 in a closed or second configuration, in which the suture is cinched and cut.

The medical device 500 may include an elongated shaft 514, a sleeve 530, a cutter 540, a cinch sleeve 550, a cinch member 570, and an elongated inner shaft 564 extending through and longitudinally movable through all of the elements. The elongated inner shaft 564 may be identical to the inner shaft 164 described above. The other elements of the medical device 500 may be similar to those discussed above except that instead of the sleeve being releasably connected to the cinch sleeve, in this example the cutter 540 is releasably connected to the cinch sleeve 550 with a snap fit.

As shown in the illustrated example, the distal end of the shaft 514 is attached to a coupler 520 and the coupler 520 is attached to the proximal end of the sleeve 530. The coupler 520, cutter stop 523 on the coupler 520, and movement limiter 541 on the cutter 540 may have the same structure and function as the coupler 320, cutter stop 323, and movement limiter 342 discussed above with regard to the device 300 shown in FIG. 7.

The cutter 540 may releasably engage the cinch sleeve 550 with a snap fit. The distal region 543 of the cutter 540 may include a first snap connector 542 and the proximal region of the cinch sleeve 550 may include a second snap connector 551 configured to releasably engage the first snap connector 542 in a snap fit. In some examples, one of the first snap connector 542 or second snap connector 551 is a protrusion and the other is a groove or recess configured to receive the protrusion. The first snap connector 542 may be disposed on the outer surface of the cutter 540 and the second snap connector 551 may be disposed on an inner surface of the cinch sleeve 550.

FIGS. 12-13 illustrate the steps involved in securing and cutting a suture using the medical device 500. The medical device 500 is assembled into the deployment or first configuration shown in FIGS. 11 and 12. In the first configuration, the inner shaft 564 may extend through the shaft 514, the sleeve 530, cutter 540, cinch sleeve 550, and cinch member 570. The enlarged distal region 562 of the inner shaft 564 may be disposed within the distal section 577 of the cinch member lumen 576, within the distal head 572, holding the cinch member 570 distally away from the distal end 558 cinch sleeve 550.

The cutter 540 is coupled to the cinch sleeve 550 with the above described snap fit such that the opening 549 of the cutter 540 is aligned under the opening 539 in the sleeve 530. With the device 500 in the first configuration, a suture 5 may be loaded into the device 500. For example, following a suturing procedure in which a first end 4 of the suture 5 is disposed within the tissue, the second, or free end 6 of the suture 5 may be fed into the distal end 558 of the cinch sleeve 550, through the cinch lumen 556 and the cutter lumen 546, and out through the aligned openings 549, 539 in the cutter 540 and sleeve 530, respectively, as shown in FIG. 12. This may be done with or without using a tool or guide, such as a tubular guide, wire, loop, needle, or the like.

The suture 5 may then be secured by moving the cinch member 570 into the cinch lumen 556. This may be achieved by pulling the inner shaft 564 proximally. A first stage of proximal longitudinal movement of the inner shaft 564 pulls the engaged cinch member 570 into the cinch lumen 556 of the cinch sleeve 550 until the proximal portion 575 of the cinch member 570 engages the cinch lumen 556 in an interference fit, thereby compressing and securing the suture 5 between the proximal portion 575 of the cinch member 570 and the inner surface of the cinch sleeve 550.

In a second stage of proximal longitudinal movement, the inner shaft 564 may then be pulled further proximally, pulling the inner shaft 564 through and proximally out of the cinch member 570. The enlarged distal region 562 moves through the lumen 546 of the cutter 540 until it engages the inner protrusion 547. Further proximal movement of the inner shaft 564 pulls the cutter 540 proximally and unsnaps the first snap connector 542 from the second snap connector 551, thereby releasing the connected cinch member 170 and cinch sleeve 550 from the cutter 540. As the cutter 540 moves proximally, the cutting surface 545 compresses the suture 5 between the proximal end of the opening 539 and the cutting surface 545, which cuts the suture 5, as shown in FIG. 13. At this point, the shaft 514, sleeve 530, cutter 540, and inner shaft 564 may be removed from the body, leaving the connected cinch member 570 and cinch sleeve 550 securing the suture 5 within the body.

Figure 14:
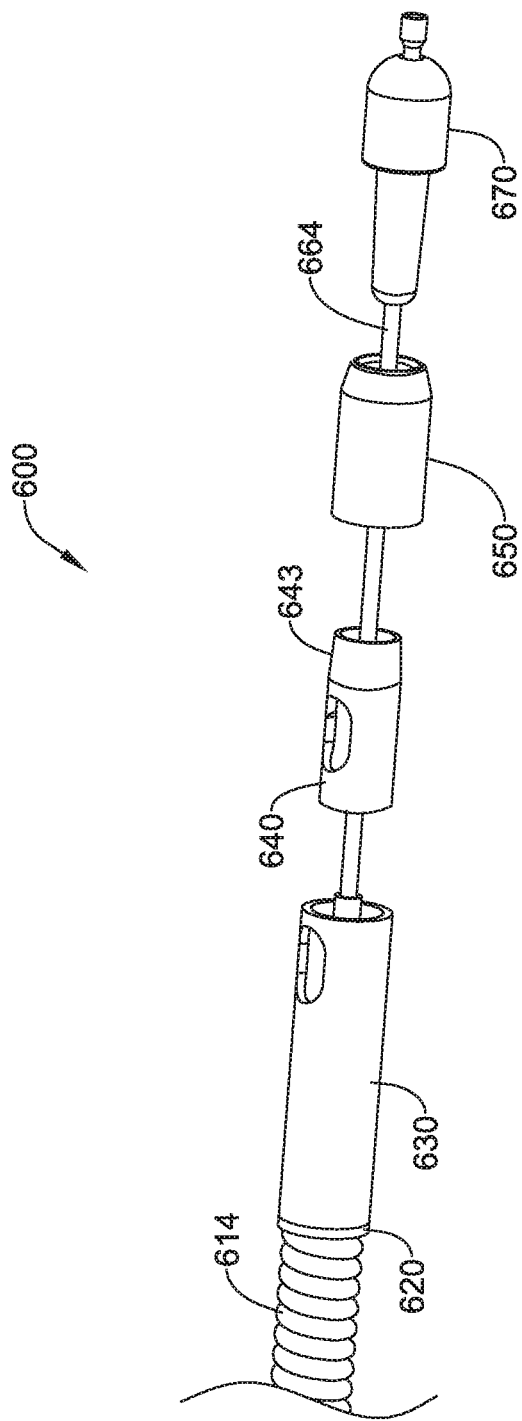
FIG. 14 is a perspective exploded view of a portion of another medical device for cinching and cutting a suture.
Figure 15:
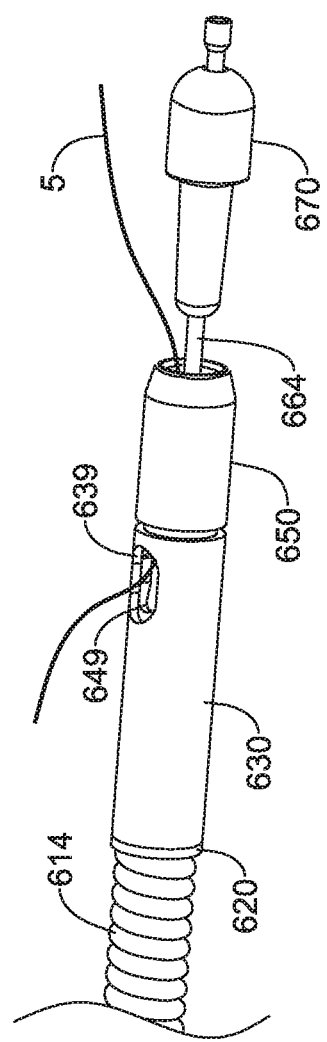
FIG. 15 is a perspective view of the medical device as shown in FIG. 14, in a first configuration.
Figure 16:
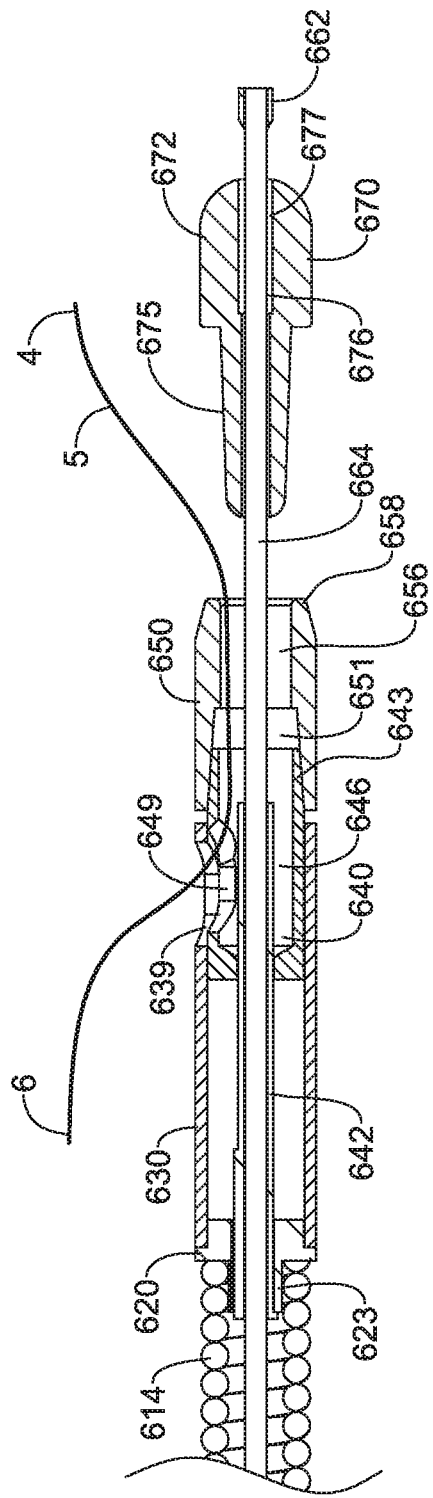
FIG. 16 is a side cross-sectional view of the medical device as shown in FIG. 14, in the first configuration.
Figure 17:
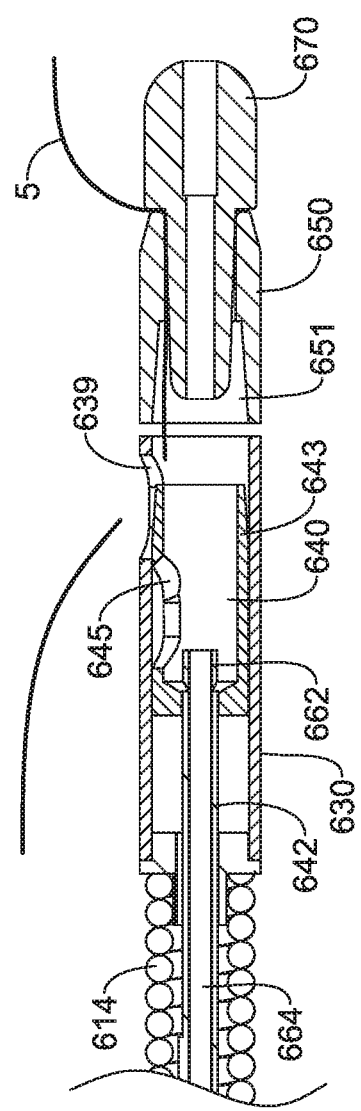
FIG. 17 is a side cross-sectional view of the medical device as shown in FIG. 14, in a second configuration.

FIGS. 14-17 illustrate another example medical device 600 for securing and cutting a suture. FIG. 14 shows a partial exploded view of the medical device 600, FIGS. 15 and 16 show the medical device 600 in an open or first configuration, allowing a suture 5 to be inserted, and FIG. 17 shows the medical device 600 in a closed or second configuration, in which the suture is cinched and cut.

The medical device 600 may include an elongated shaft 614, a sleeve 630, a cutter 640, a cinch sleeve 650, a cinch member 670, and an elongated inner shaft 664 extending through and longitudinally movable through all of the elements. The elongated inner shaft 664 may be identical to the inner shaft 164 described above. The other elements of the medical device 600 may be similar to those discussed above except that instead of the sleeve being releasably connected to the cinch sleeve, in this example the cutter 640 is releasably connected to the cinch sleeve 650 with a friction fit.

As shown in the illustrated example, the distal end of the shaft 614 is attached to a coupler 620 and the coupler 620 is attached to the proximal end of the sleeve 630. The coupler 620 and cutter stop 623 on the coupler 620 may have the same structure and function as the coupler 320 and cutter stop 323 discussed above with regard to the device 300 shown in FIG. 7. The movement limiter 642 on the cutter 640 in the example shown in FIG. 16 is an elongate tube extending into the cutter lumen 646 when the cutter 640 is in the first configuration.

The cutter 640 may releasably engage the cinch sleeve 650 with a friction or interference fit. The cutter 640 may define a distal tapered region 643 and the proximal region of the cinch sleeve 650 may define a proximal tapered section 651 of the cinch lumen 656 configured to releasably engage the distal tapered region 643. In some examples, the distal tapered region 643 may define a distal taper of between 2 degrees and 10 degrees. In other examples, the taper may be between 3 degrees and 6 degrees. In further examples, the taper may be 4 degrees. The distal region of the cinch lumen 656 may be substantially cylindrical.

FIGS. 15-17 illustrate the steps involved in securing and cutting a suture using the medical device 600. The medical device 600 is assembled into the deployment or first configuration shown in FIGS. 15 and 16. In the first configuration, the inner shaft 664 may extend through the shaft 614, the sleeve 630, cutter 640, cinch sleeve 650, and cinch member 670. The enlarged distal region 662 of the inner shaft 664 may be disposed within the distal section 677 of the cinch member lumen 676, within the distal head 672, holding the cinch member 670 distally away from the distal end 658 cinch sleeve 650.

The cutter 640 is coupled to the cinch sleeve 650 with the above described friction or interference fit such that the opening 649 of the cutter 640 is aligned under the opening 639 in the sleeve 630. With the device 600 in the first configuration, a suture 5 may be loaded into the device 600. For example, following a suturing procedure in which a first end 4 of the suture 5 is disposed within the tissue, the second, or free end 6 of the suture 5 may be fed into the distal end 658 of the cinch sleeve 650, through the cinch lumen 656 and the cutter lumen 646, and out through the aligned openings 649, 639 in the cutter 640 and sleeve 630, respectively, as shown in FIG. 16. This may be done with or without using a tool or guide, such as a tubular guide, wire, loop, needle, or the like.

The suture 5 may then be secured by moving the cinch member 670 into the cinch lumen 656. This may be achieved by pulling the inner shaft 664 proximally. A first stage of proximal longitudinal movement of the inner shaft 664 pulls the engaged cinch member 670 into the cinch lumen 656 of the cinch sleeve 650 until the distal head 672 engages the cinch sleeve 650, thereby compressing and securing the suture 5 between the proximal portion 675 of the cinch member 670 and the inner surface of the cinch sleeve 650. The cinch member 670 is shown positioned completely within the cinch sleeve 650, however, as discussed above with regard to FIG. 3, in some examples, the cinch member 670 may secure the suture 5 when a gap remains between the head of the cinch member 670 and the distal end of the cinch sleeve 650.

In a second stage of proximal longitudinal movement, the inner shaft 664 may then be pulled further proximally, pulling the inner shaft 664 through and proximally out of the cinch member 670. The enlarged distal region 662 moves through the lumen 646 of the cutter 640 until it engages the distal end of the elongated tubular movement limiter 642. Further proximal movement of the inner shaft 664 overcomes the friction or interference between the distal tapered region 643 of the cutter 640 and the proximal tapered section 651 of the cinch lumen 656, and pulls the cutter 640 proximally, thereby releasing the connected cinch member 670 and cinch sleeve 650 from the cutter 640. As the cutter 640 moves proximally, the cutting surface 645 compresses the suture 5 between the proximal end of the opening 639 and the cutting surface 645, which cuts the suture 5, as shown in FIG. 17. At this point, the shaft 614, sleeve 630, cutter 640, and inner shaft 664 may be removed from the body, leaving the connected cinch member 670 and cinch sleeve 650 securing the suture 5 within the body.

Figure 18:
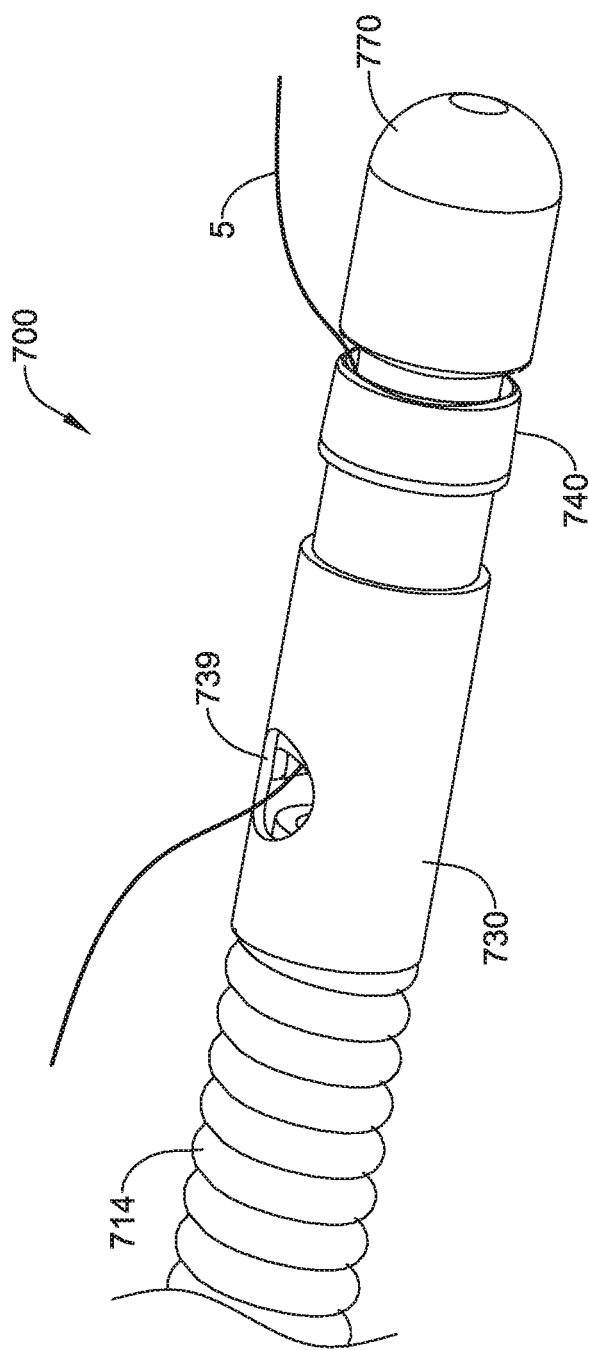
FIG. 18 is a perspective view of a portion of another medical device for cinching and cutting a suture.
Figure 19:
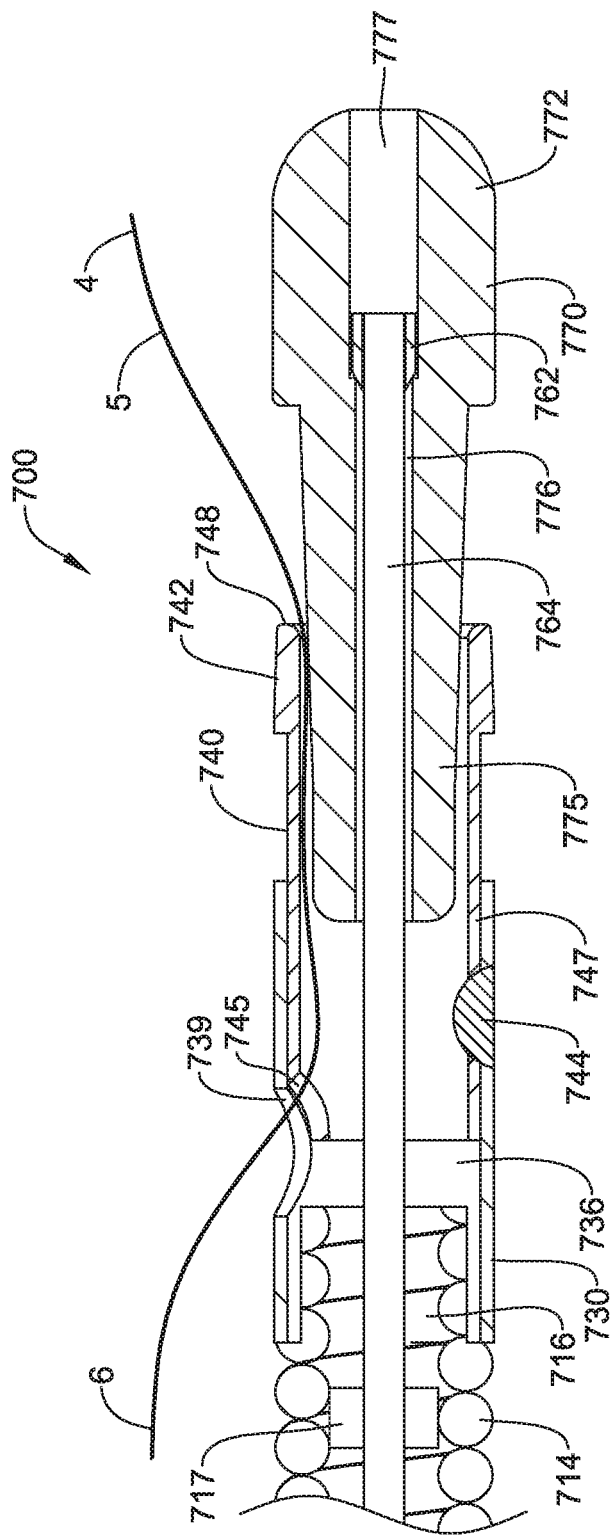
FIG. 19 is a side cross-sectional view of the medical device as shown in FIG. 18, in a first configuration.
Figure 20:
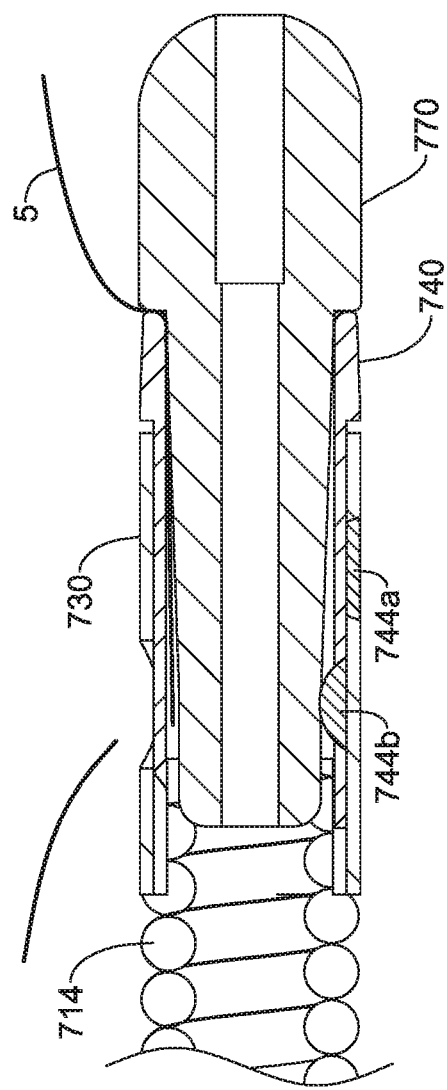
FIG. 20 is a side cross-sectional view of the medical device as shown in FIG. 18, in a second configuration.

FIGS. 18-20 illustrate another example medical device 700 for securing and cutting a suture. FIGS. 18 and 19 show the medical device 700 in an open or first configuration, allowing a suture 5 to be inserted, and FIG. 20 shows the medical device 700 in a closed or second configuration, in which the suture is cinched and cut.

The medical device 700 may include an elongated shaft 714, a sleeve 730, a cutter 740, a cinch member 770, and an elongated inner shaft 764 extending through and longitudinally movable through all of the elements. The elongated inner shaft 764 may be identical to the inner shaft 164 described above. The shaft 714, sleeve 730, and cinch member 770 may be similar to those discussed above with the cutter 740 having a different structure as described below.

As shown in the illustrated example, the distal end of the shaft 714 is attached directly to the sleeve 730. In other examples, a coupler such as coupler 520 may be attached to the distal end of the shaft 714 and the proximal end of the sleeve 730. The sleeve 730 may define an opening 739 extending into the sleeve lumen 736.

The cutter 740 may be releasably coupled to the sleeve 730. In some examples, the cutter 740 may have a proximal region 747 disposed within the sleeve lumen 736, and an enlarged distal head 742 spaced away from the distal end of the sleeve 730 when the device 700 is in the first configuration. The cutter 740 may have a cutting surface 745 disposed at the proximal end of the cutter 740. The cutting surface 745 may be on a cut-out or skived region of the proximal end of the cutter 740. In the illustrated example, the cutting surface 745 is a discrete region on the circumference of the cutter proximal end. In some examples, the cutter 740 may be releasably coupled to the sleeve 730 by a frangible connection 744 in the first configuration. The frangible connection 744 may be a spot weld or soldered connection that is broken by pulling the cutter 740 proximally. The frangible connection 744 holds the cutter 740 in place relative to the sleeve 730 during delivery of the device 700 to the desired location within the body and during insertion of the suture 5 into the device 700.

FIGS. 18-20 illustrate the steps involved in securing and cutting a suture using the medical device 700. The medical device 700 is assembled into the deployment or first configuration shown in FIGS. 18 and 19. In the first configuration, the inner shaft 764 may extend through the shaft 714, the sleeve 730, cutter 740, and cinch member 770. The enlarged distal region 762 of the inner shaft 764 may be disposed within the distal section 777 of the cinch member lumen 776, within the distal head 772, holding at least the distal head 772 of the cinch member 770 distally away from the distal end 748 of the cutter 740.

The cutter 740 is coupled to the sleeve 730 with the above described frangible connection 744 such that the cutting surface 745 of the cutter 740 is disposed under or distal of the opening 739 in the sleeve 730. With the device 700 in the first configuration, a suture 5 may be loaded. For example, following a suturing procedure in which a first end 4 of the suture 5 is disposed within the tissue, the second, or free end 6 of the suture 5 may be fed into the distal end 748 of the cutter 740, through the cutter lumen 746, and out through the opening 739 in the sleeve 730, as shown in FIG. 19. This may be done with or without using a tool or guide, such as a tubular guide, wire, loop, needle, or the like.

The suture 5 may then be secured by moving the cinch member 770 into the cutter lumen 746. This may be achieved by pulling the inner shaft 764 proximally. In a first stage of proximal longitudinal movement, the inner shaft 764 pulls the engaged cinch member 770 into the cutter lumen 746 until the distal head 772 engages the distal end 748 of the cutter 740, thereby compressing and securing the suture 5 between the proximal portion 775 of the cinch member 770 and the inner surface of the cutter 740. The cinch member 770 is shown positioned completely within the cinch sleeve 750 in FIG. 20, however, as discussed above with regard to FIG. 3, in some examples, the cinch member 770 may secure the suture 5 when a gap remains between the distal head 772 of the cinch member 770 and the distal end 748 of the cinch sleeve 750.

With the distal head 772 of the cinch member 770 engaged with the distal end 748 of the cutter, in a second stage of proximal longitudinal movement, the inner shaft 764 may be pulled further proximally, breaking the frangible connection 744, thereby releasing the cutter 740 from the sleeve 730. Once the frangible connection 744 is broken, further proximal movement of the inner shaft 764 moves the cutter 740 proximally, compressing the suture 5 between the proximal end of the opening 739 and the cutting surface 745, which cuts the suture 5, as shown in FIG. 20. In some examples, breaking the frangible connection 744 may result in the connection being separated into two sections 744a, 744b, with section 744a remaining attached to the sleeve 730 and second 744b remaining attached to the cutter 740 as shown in FIG. 20.

Continued proximal movement of the inner shaft 764 through and proximally out of the cinch member 770. The enlarged distal region 762 moves proximally through the lumen 746 of the cutter 740 until it engages a restriction element 717 disposed within the distal region of the shaft lumen 716. Further proximal movement of the inner shaft 764

At this point, the shaft 514, sleeve 530, cutter 540, and inner shaft 564 may be removed from the body, leaving the connected cinch member 570 and cinch sleeve 550 securing the suture 5 within the body.

Figure 21:
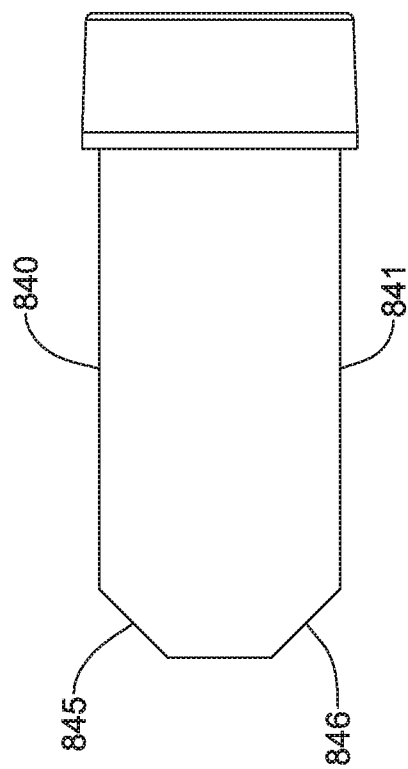
FIG. 21 is a side cross-sectional view of an alternate cutter for the medical device as shown in FIG. 18.

FIG. 21 illustrates an alternate cutter 840 for use with the medical device 700 discussed above. The cutter 740 described above has a cutting surface 745 disposed on a discrete region of the circumference, such that the cutting surface 745 is only present in the region of the opening 739 in the sleeve 730. The alternate cutter 840 is the same as the cutter 740 except for the cutting surface. The cutter 840 includes a cutting surface 845 that extends around the entire circumference of the proximal end of the cutter 840. In the illustrated example, the cutting surface 845 is formed on a proximally facing angled edge 846 of the cutter 840. The angled edge 846 may be at an angle of between 35 degrees and 55 degrees relative to the outer surface 841 of the cutter 840. In some examples, the angled edge 846 may be at a 45 degree angle. As with the cutter 740 described above, the cutter 840 may be releasably connected to the sleeve 730 with a frangible connection 744 such as a spot weld. When the frangible connection 744 is broken and the cutter 840 is moved proximally, the cutting surface 845 engages and cuts the suture 5 regardless of the rotational orientation of the cutter 840 within the sleeve 730.

Figure 22:
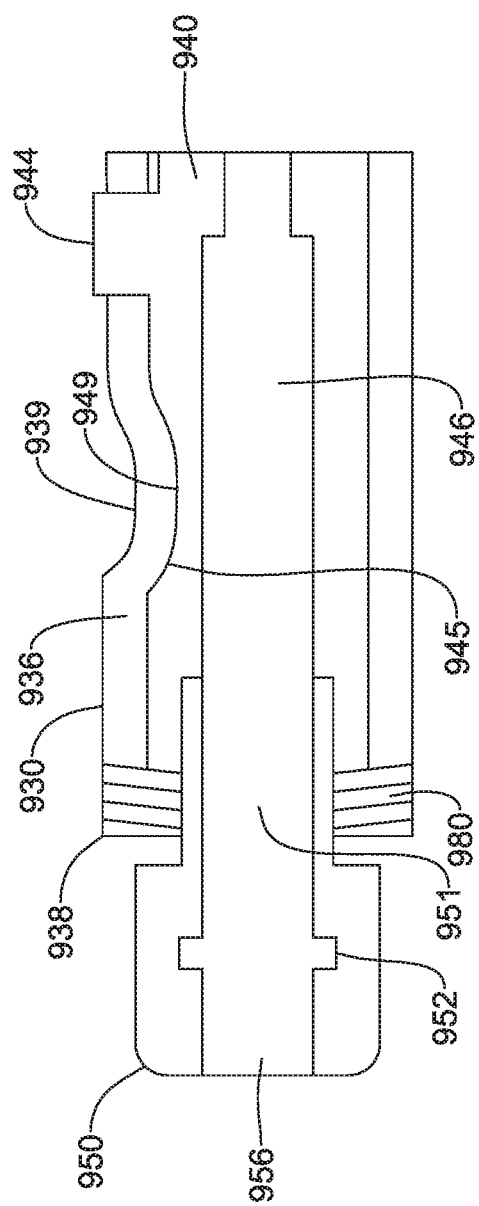
FIG. 22 is a side cross-sectional view of a portion of another medical device for cinching and cutting a suture.
Figure 23:
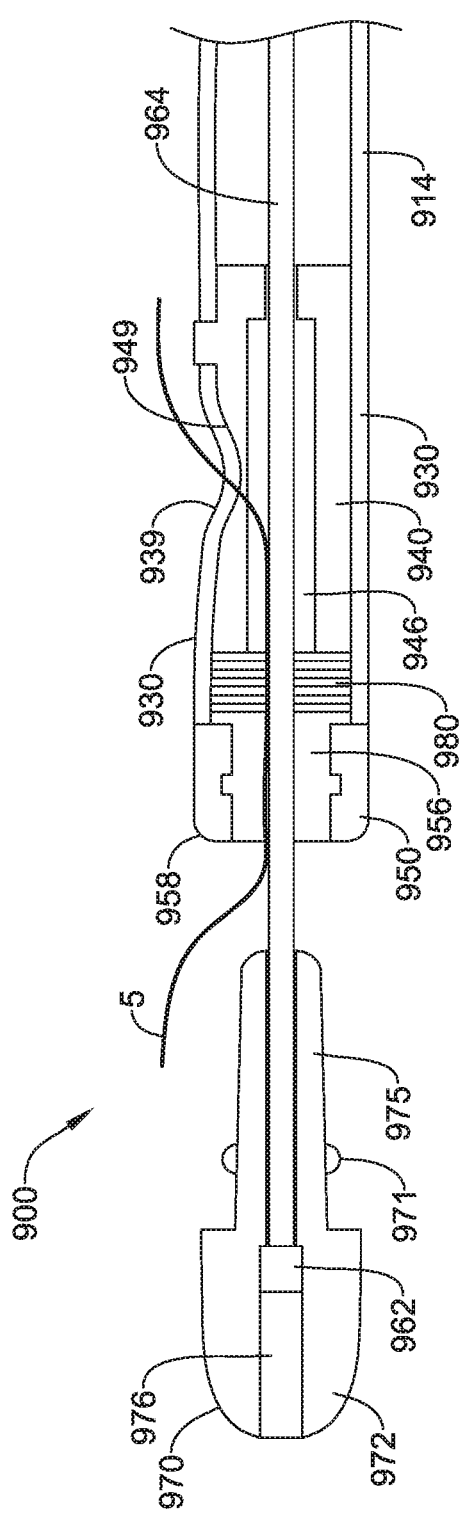
FIG. 23 is a side cross-sectional view of the medical device as shown in FIG. 22, in a first configuration.

FIGS. 22-27 illustrate portions of another medical device 900 for cinching and cutting a suture. The medical device 900 may include a sleeve 930 having a sleeve lumen 936, a cinch sleeve 950 having a cinch lumen 956, a cutter 940 having a cutter lumen 946, and a cinch member 970 having a cinch member lumen 976. An elongated inner shaft 964 may extend through and be longitudinally movable through the sleeve lumen 936, cutter lumen 946, cinch lumen 956, and cinch member lumen 976, as shown in FIG. 23. The elongated inner shaft 964 may be the same as the elongated inner shaft 164 described above.

Figure 24:
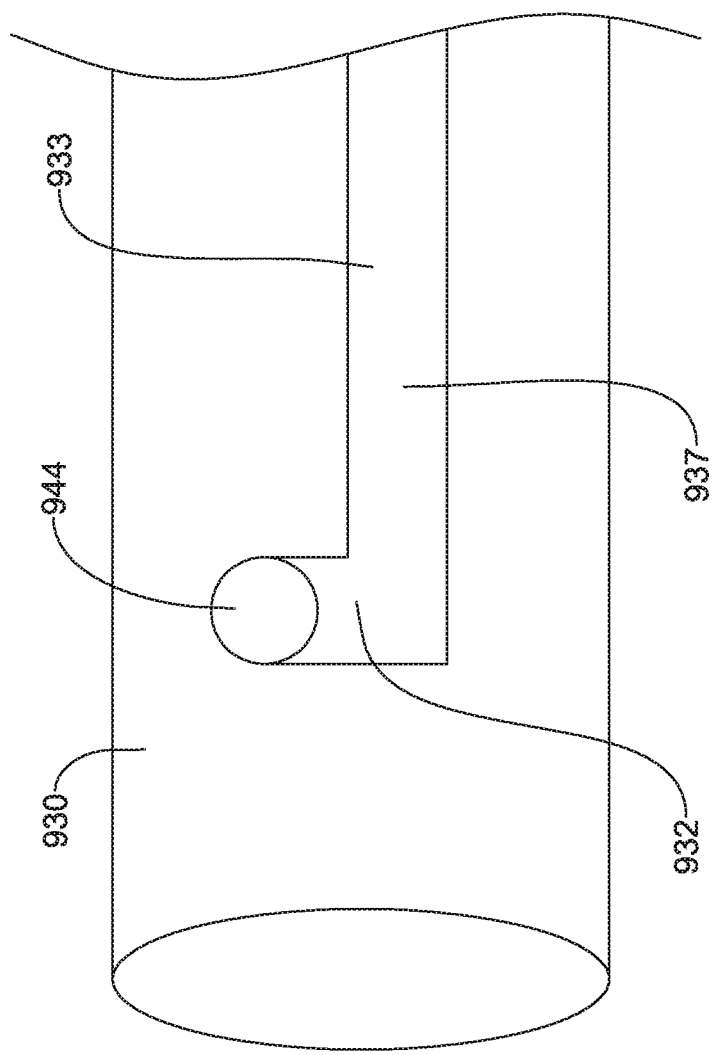
FIG. 24 is a top view of a portion of the medical device as shown in FIG. 23, in the first configuration.

In some examples, a shaft 914 similar to the shaft 114 described above, may be attached directly to the proximal end of the sleeve 930 by threading, adhesive, welding, soldering, or other suitable connection method. The sleeve 930 may have an opening 939 extending into the sleeve lumen 936, and a distal end 938 with a reduced diameter. The sleeve 930 may further include a slot 937 extending into the sleeve lumen 936. The slot 937 may include a first section 932 extending circumferentially along a portion of the sleeve 930, and a second section 933 extending axially along the sleeve 930, as shown in FIG. 24.

The cinch sleeve 950 may have a proximal end 951 releasably coupled to the distal end of the cutter 940. In some examples, the proximal end 951 may engage the cutter 940 with a press fit, interference fit, or snap fit. In some examples, the proximal end 951 of the cinch sleeve 950 may define a reduced diameter region. A compression spring 980 may be disposed between the cutter 940 and the distal end 938 of the sleeve 930. The compression spring 980 may be placed over the reduced diameter proximal end 951, as shown in FIG. 22. The proximal end of the cutter 940 may include an outwardly extending cutter pin 944 configured to slide within the slot 937 in the sleeve 930. In a first, locked configuration, the cutter pin 944 resides in the first section 932 of the slot 937, as shown in FIG. 24. In this configuration, the cutter 940 is locked in a distal position, compressing the compression spring 980 against the distal end of the sleeve 930, as shown in FIG. 23.

The cutter 940 may include an opening 949 into the cutter lumen 946. A shear edge or cutting surface 945 may be defined on the opening. In some embodiments, a cutting surface may also be defined on the proximal edge of the opening 939 in the sleeve (not shown). In some examples, the cutting surface 945 is disposed on the distal edge of the opening 949. When the device 900 is in the first configuration, shown in FIG. 23, the opening 949 in the cutter 940 is aligned under the opening 939 on the sleeve 930.

The cinch member 970 may be the same as the cinch member 170 described above, but with the addition at least one projection 971 on the proximal portion 975 configured to engage at least one recess 952 in the cinch lumen 956 which secures the cinch member 970 within the cinch sleeve 950.

FIGS. 23-27 illustrate the steps involved in securing and cutting a suture using the medical device 900. The medical device 900 is assembled into the deployment or first configuration shown in FIGS. 22-24. In the first configuration, the inner shaft 964 may extend through the sleeve 930, cutter 940, cinch sleeve 950, and cinch member 970. The enlarged distal region 962 of the inner shaft 964 may be disposed within the distal head 972, holding the cinch member 970 distally away from the cinch sleeve 950, as shown in FIG. 23.

The cutter 140 is disposed in a distalmost position, compressing the compression spring 980 against the distal end 938 of the sleeve 930, with the cutter pin 944 residing in the first section 932 of the slot 937 to lock the cutter 940 in place, as shown in FIG. 24. In this position, the opening 949 of the cutter 940 is aligned under the opening 939 in the sleeve 930, as shown in FIG. 23.

With the device 900 in the first configuration, a suture 5 may be loaded into the device 900. The suture 5 may be fed into the distal end 958 of the cinch sleeve 950, through the cinch lumen 956 and the cutter lumen 946, and out through the aligned openings 949, 939 in the cutter 940 and sleeve 930, respectively. This may be done with or without using a tool or guide, such as a tubular guide, wire, loop, needle, or the like.

Figure 25:
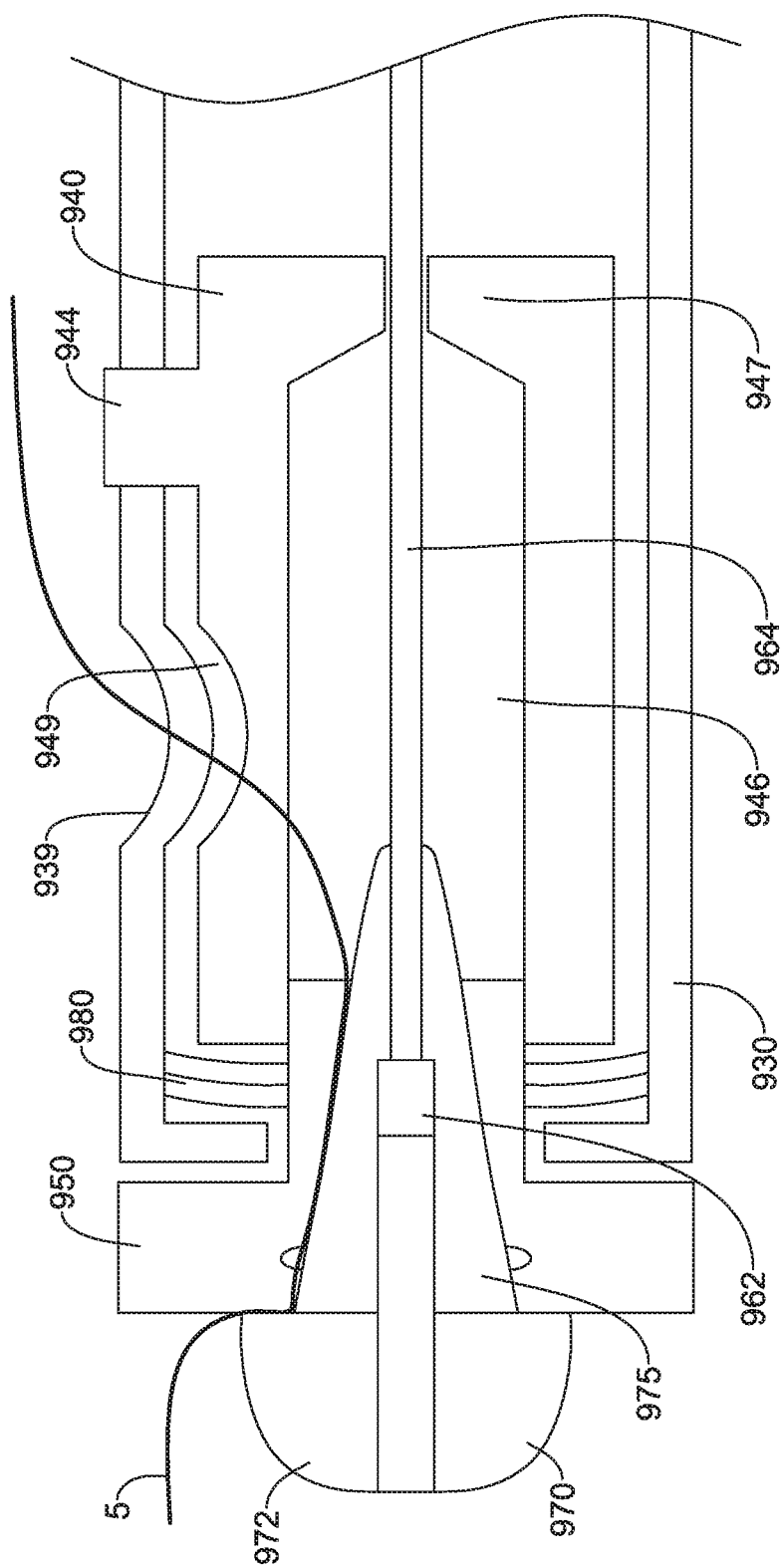
FIG. 25 is a side cross-sectional view of the medical device as shown in FIG. 23, in a second configuration.

Once the suture 5 is disposed within the cinch lumen 956, the suture 5 may be secured by moving the cinch member 970 into the cinch lumen 956. This may be achieved by pulling the inner shaft 964 proximally. A first stage of proximal longitudinal movement of the inner shaft 964 pulls the engaged cinch member 970 into the cinch lumen 956 until the projection 971 engages the recess 952 and distal head 972 engages the cinch sleeve 950, thereby compressing and securing the suture 5 between the proximal portion 975 of the cinch member 970 and the inner surface of the cinch sleeve 950, and between the distal end 958 of the cinch sleeve 950 and the distal head 972, moving the device 900 into a second configuration as shown in FIG. 25.

Figure 26:
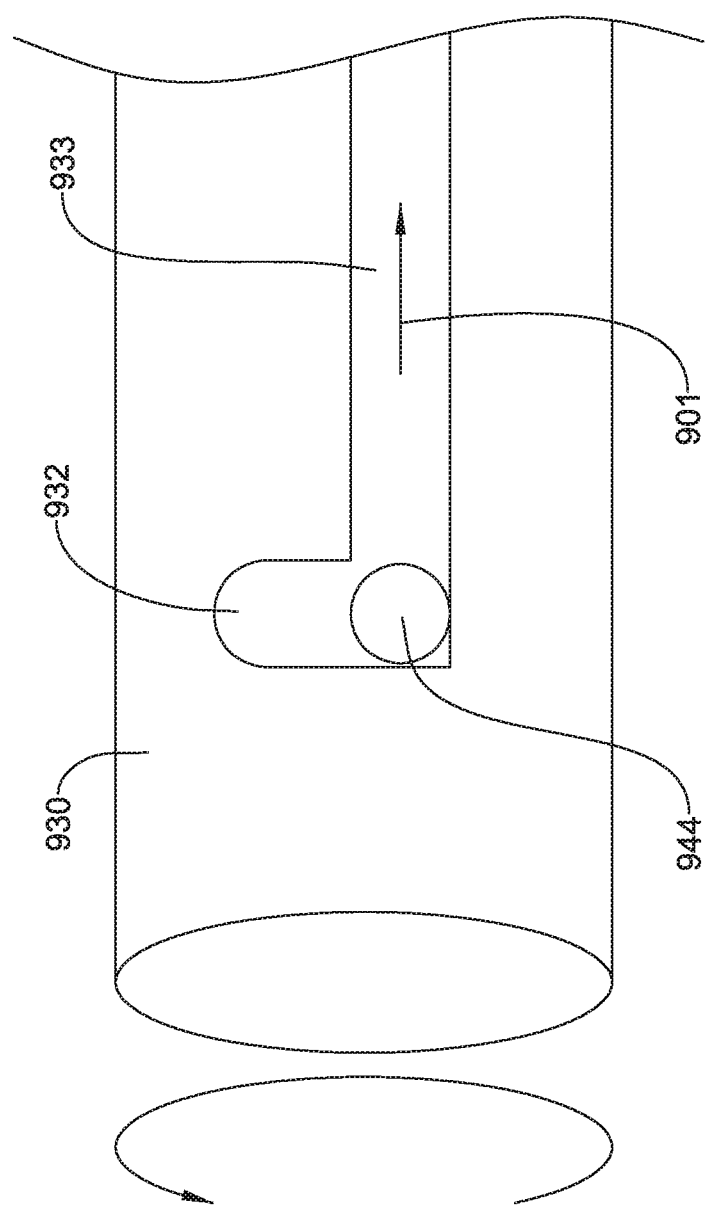
FIG. 26 is a top view of a portion of the medical device as shown in FIG. 23, in the second configuration.

In a second stage of proximal longitudinal movement, the inner shaft 964 may then be pulled further proximally, pulling the inner shaft 964 through and proximally out of the cinch member 970. The engagement between the projection 971 and recess 952 locks the cinch member 970 to the cinch sleeve 950. The enlarged distal region 962 moves through the lumen 946 of the cutter 940 until it engages an inner protrusion 947 extending into the lumen 946. In the next step, either the sleeve 930 or the cutter 940 is rotated to move the cutter pin 944 out of the first section 932 and into the second section 933 of the slot 937. The sleeve 930 may be rotated, as shown in FIG. 26, by rotating the shaft which is attached to the sleeve 930. The cutter 940 may be rotated by rotating the inner shaft 964. The enlarged distal region 962 of the inner shaft 964 is engaged with the inner protrusion 947 of the cutter, thus rotation of the inner shaft 964 is translated to rotation of the cutter 940. Once the cutter pin 944 is in the second section 933 of the slot 937, the compression spring 980 is free to expand to its biased, expanded configuration, which pushes the cutter 940 and cutter pin 944 proximally, as indicated by arrow 901 in FIG. 26. As the compression spring 980 expands and the cutter 940 moves proximally, the suture 5 is compressed and cut by the cutting surface 945 on the opening 949 moving under and proximally past the opening 939 in the sleeve. See FIG. 27.

Figure 27:
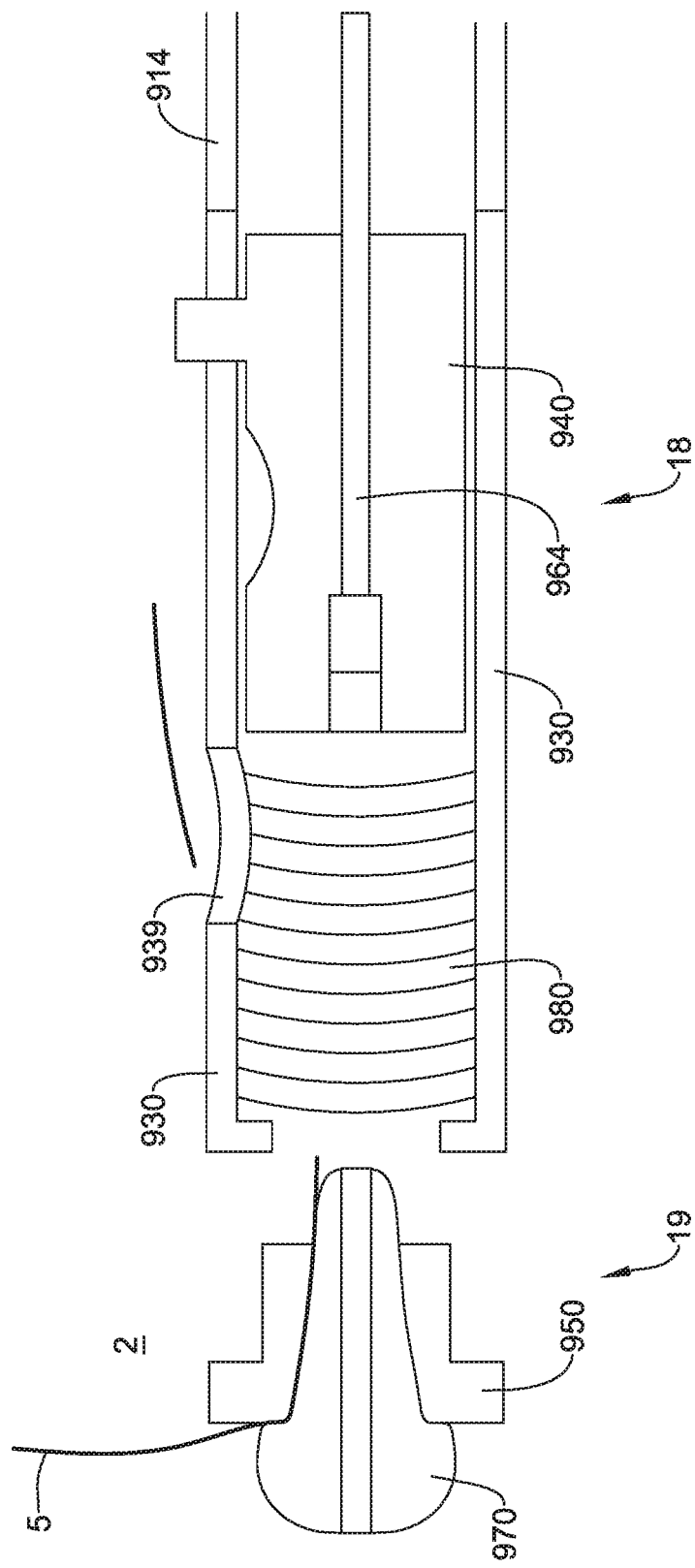
FIG. 27 is a side cross-sectional view of the medical device as shown in FIG. 23, in a separated configuration.

The shaft 914, sleeve 930, compression spring 980, cutter 940, and inner shaft 964 remain connected to one another, forming a shaft assembly 18, which may be removed from the body. The cinch member 970 and cinch sleeve 950 form a cinch assembly 19, and may be left in place adjacent the tissue 2 with the secured suture 5, as shown in FIG. 27. The suture 5 is embedded in the tissue 2 and secured adjacent the tissue 2 by the cinch assembly 19.

Figure 28:
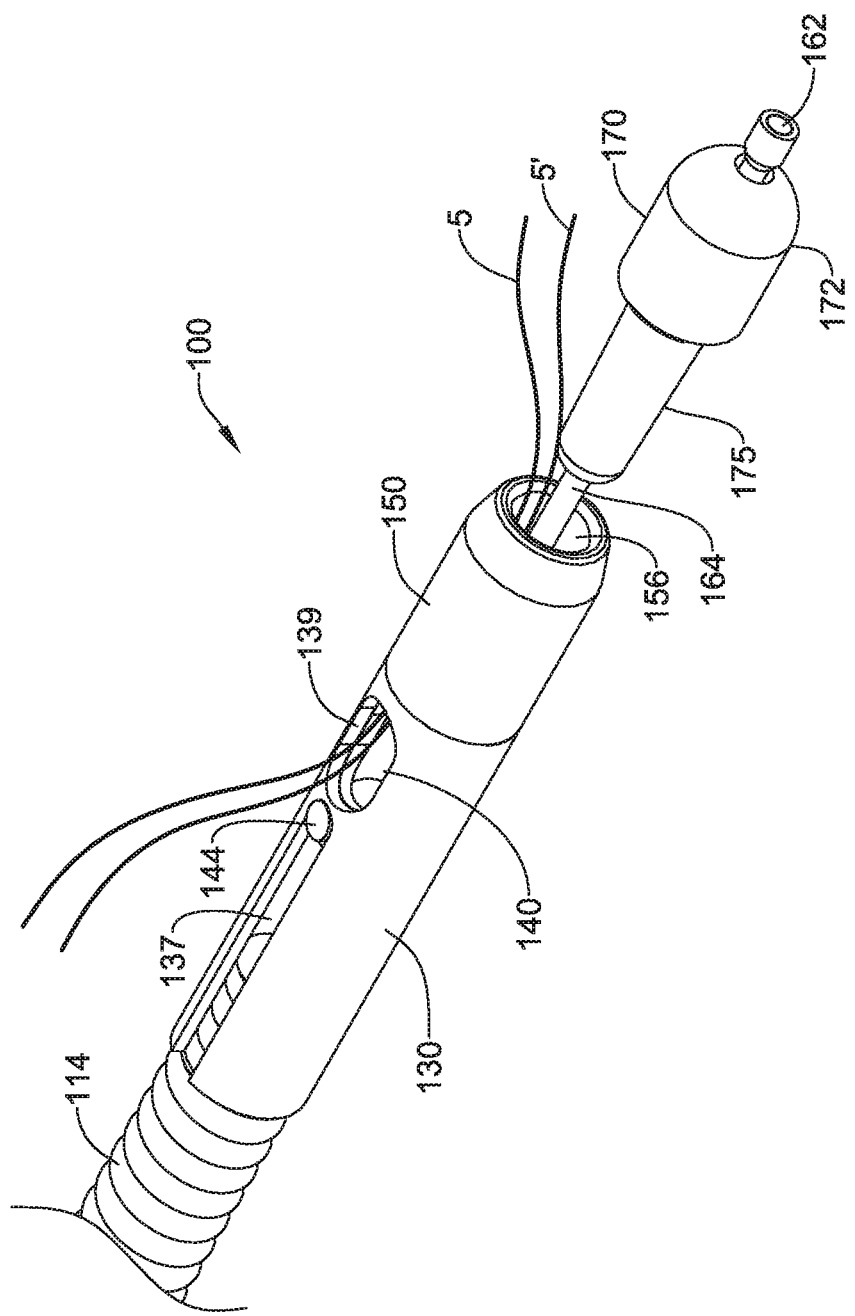
FIG. 28 is the portion of an example medical device as shown in FIG. 2, with two sutures extending therethrough.

In the above discussion, the various example medical devices are described as being used to secure "a" suture and the figures illustrate a single suture 5 being secured and cut with the devices. It will be understood that any of the medical devices described herein may be used to secure and cut any number of sutures including one, two, three, four, five, etc. FIG. 28 illustrates the device 100 shown in FIG. 1, but here with two sutures 5, 5' threaded through the cinch lumen 156 and cutter lumen to the openings 149, 139.

The materials that can be used for the various components of the medical devices disclosed herein may include those commonly associated with medical devices. Any of the devices, members and/or components of members or devices disclosed herein may be made from a metal, metal alloy, polymer (some examples of which are disclosed below), a metal-polymer composite, ceramics, combinations thereof, and the like, or other suitable material or composites of materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments polymers can be blended with a liquid crystal polymer (LCP). For example, the mixture can contain up to about 6 percent LCP.

Some examples of suitable metals and metal alloys include stainless steel, such as 304V, 304L, 316LV, and 17-7 stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for cinching and cutting one or more suture, the medical device comprising:
   a shaft defining a shaft lumen;
   a sleeve having a sleeve lumen, the sleeve attached to the shaft;
   a cutter slidable within the sleeve lumen, the cutter including a distal portion;
   a cinch sleeve defining a cinch lumen, the cinch sleeve including a proximal portion configured to receive the distal portion of the cutter within the cinch lumen such that the cinch sleeve is releasably coupled to the cutter;
   a cinch member defining a cinch member lumen, the cinch member including at least a proximal portion configured to fit within the cinch lumen; and
   an inner shaft extending through and longitudinally movable within the shaft lumen, the sleeve lumen, the cinch lumen, and the cinch member lumen;
   wherein at least one of the cutter and sleeve define a cutting surface, wherein the cutter is slidable between a distal position configured to allow one or more suture to be loaded into the medical device, and a proximal position configured to cut the one or more suture.

2. The medical device of claim 1, wherein the cutter has a cutter lumen with a cutter opening extending into the cutter lumen, and the sleeve has a sleeve opening extending into the sleeve lumen, wherein when the cutter is in the distal position, the cutter opening and sleeve opening are aligned, and when the cutter is in the proximal position, the cutter opening is proximal of the sleeve opening.

3. The medical device of claim 2, wherein when the cutter is in the distal position, a suture pathway is formed extending through the cinch lumen and cutter lumen, and out through the aligned cutter and sleeve openings.

4. The medical device of claim 1, wherein a distal end of the inner shaft is configured to releasably engage the cinch member lumen, wherein proximal longitudinal movement of the inner shaft moves the cinch member from a first configuration in which at least a part of the cinch member is spaced apart from a distal end of the cinch sleeve, to a second configuration in which the proximal portion of the cinch member engages the cinch lumen.

5. The medical device of claim 4, wherein the cinch member lumen has a distal section and a proximal section, wherein a diameter of the distal section is larger than a diameter of the proximal section, wherein the distal end of the inner shaft has a diameter larger than the diameter of the proximal section of the cinch member lumen, wherein the distal end is compressible such that application of a predetermined amount of proximal longitudinal force compresses the distal end, allowing it to move into the proximal section of the cinch member lumen.

6. The medical device of claim 5, wherein the cutter has a protrusion extending into a lumen of the cutter, the protrusion configured to engage the distal end of the inner shaft, wherein from the second configuration, further proximal longitudinal movement of the inner shaft moves the distal end through and out of the cinch member lumen and into engagement with the protrusion such that continued proximal longitudinal movement of the inner shaft moves the cutter from the distal position to the proximal position and releases the cutter from the cinch sleeve.

7. The medical device of claim 1, wherein the shaft includes a distal compressible coil attached to a proximal end of the cutter, wherein the compressible coil limits distal and proximal movement of the cutter.

8. The medical device of claim 1, further comprising a coupler attached to a distal end of the shaft and a proximal end of the sleeve, the coupler including a cutter stop configured to receive a movement limiter fixed to a proximal end of the cutter in a sliding engagement, wherein distal movement of the cutter is limited by engagement between the movement limiter and the cutter stop.

9. The medical device of claim 1, wherein the cinch sleeve is releasably coupled to the sleeve via a releasable connection between the cinch sleeve and the cutter.

10. The medical device of claim 1, wherein the distal portion of the cutter has a first snap connector and the proximal portion of the cinch sleeve has a second snap connector configured to releasably engage the first snap connector.

11. The medical device of claim 1, further comprising a compressible spring disposed between a distal end of the cutter and a distal end of the sleeve, wherein when the cutter is in the distal position, the cutter compresses the compressible spring, and when the cutter is in the proximal position the compressible spring is in a biased expanded configuration.

12. The medical device of claim 1, wherein the cinch member includes at least one protrusion on the proximal portion and the cinch sleeve includes at least one recess on an inner surface of the cinch lumen, the at least one recess configured to receive the at least one protrusion to lock the cinch member to the cinch sleeve.

13. The medical device of claim 1, wherein the sleeve includes a slot having a first section and a second section, and the cutter includes a pin configured to move between the first and second sections.

14. The medical device of claim 13, wherein the pin is in the first section when the cutter is in the distal position, and movement of the pin into the second section causes the cutter to move to the proximal position.

15. The medical device of claim 13, wherein movement of the pin from the first section into the second section is achieved by rotating one of the sleeve and cutter relative to the other of the sleeve and cutter.

16. The medical device of claim 1, wherein the cinch sleeve is releasably coupled to the cutter via a friction fit between an inner surface of the proximal portion of the cinch sleeve and an outer surface of the distal portion of the cutter.

17. The medical device of claim 1, wherein the sleeve includes a distal end, and the distal portion of the cutter extends distally beyond the distal end of the sleeve.

18. A medical device for cinching and cutting one or more suture, the medical device comprising:
- a shaft defining a shaft lumen;
- a sleeve having a sleeve lumen, the sleeve attached to the shaft;
- a cutter slidable within the sleeve lumen;
- a cinch sleeve defining a cinch lumen, the cinch sleeve releasably coupled to the cutter, wherein the cinch sleeve is releasably coupled to the cutter via a releasable connection between the cinch sleeve and the cutter, wherein the cutter has a distal tapered region configured to engage a proximally tapered section of the cinch lumen in a friction fit;
- a cinch member defining a cinch member lumen, the cinch member including at least a proximal portion configured to fit within the cinch lumen; and
- an inner shaft extending through and longitudinally movable within the shaft lumen, the sleeve lumen, the cinch lumen, and the cinch member lumen;
- wherein at least one of the cutter and sleeve define a cutting surface, wherein the cutter is slidable between a distal position configured to allow one or more suture to be loaded into the medical device, and a proximal position configured to cut the one or more suture.

19. The medical device of claim 18, wherein the sleeve includes a distal end, and the distal region of the cutter extends distally beyond the distal end of the sleeve.

20. A medical device for cinching and cutting one or more suture, the medical device comprising:
- an elongated shaft defining a shaft lumen;
- a sleeve having a sleeve lumen and an opening extending into the sleeve lumen, the sleeve attached to the shaft;
- a cutter at least partially disposed within the sleeve lumen, the cutter releasably connected to the sleeve by a frangible connection, the cutter having a cutter lumen and defining a cutting surface;
- a cinch member defining a cinch member lumen; and
- an inner shaft extending through and longitudinally movable within the shaft lumen, the sleeve lumen, the cutter lumen, and the cinch member lumen;
- wherein the cinch member and cutter are each slidable between distal positions configured to allow one or more suture to be loaded into the medical device, and proximal positions configured to allow the cutter to cut the one or more suture;
- wherein sliding the cinch member to its proximal position breaks the frangible connection, allowing the cutter to move to its proximal position.

* * * * *